United States Patent
Ikeda

(10) Patent No.: US 9,615,726 B2
(45) Date of Patent: Apr. 11, 2017

(54) MEDICAL INSTRUMENT

(71) Applicant: OLYMPUS CORPORATION, Tokyo (JP)

(72) Inventor: Hiromu Ikeda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 151 days.

(21) Appl. No.: 14/138,769

(22) Filed: Dec. 23, 2013

(65) Prior Publication Data

US 2014/0114127 A1     Apr. 24, 2014

Related U.S. Application Data

(63) Continuation of application No. PCT/JP2012/064779, filed on Jun. 8, 2012.

(30) Foreign Application Priority Data

Jul. 22, 2011 (JP) .................................. 2011-160494

(51) Int. Cl.
| | |
|---|---|
| A61B 1/00 | (2006.01) |
| A61B 1/04 | (2006.01) |
| A61B 1/005 | (2006.01) |
| G02B 23/24 | (2006.01) |
| A61B 1/313 | (2006.01) |

(52) U.S. Cl.
CPC .......... *A61B 1/0016* (2013.01); *A61B 1/0052* (2013.01); *A61B 1/0057* (2013.01); *A61B 1/00078* (2013.01); *A61B 1/00147* (2013.01); *A61B 1/00156* (2013.01); *G02B 23/2476* (2013.01); *A61B 1/04* (2013.01); *A61B 1/313* (2013.01)

(58) Field of Classification Search
None
See application file for complete search history.

(56) References Cited

U.S. PATENT DOCUMENTS

| | | | |
|---|---|---|---|
| 6,015,420 A | 1/2000 | Wulfman et al. | |
| 6,156,048 A | 12/2000 | Wulfman et al. | |

(Continued)

FOREIGN PATENT DOCUMENTS

| | | |
|---|---|---|
| JP | 55-45426 A | 3/1980 |
| JP | H06-189898 A | 7/1994 |

(Continued)

OTHER PUBLICATIONS

Machine translation of JP 2005-329079.*
International Search Report dated Sep. 4, 2012 issued in PCT/JP2012/064779.

*Primary Examiner* — Alexandra Newton
(74) *Attorney, Agent, or Firm* — Scully, Scott, Murphy & Presser, P.C.

(57) ABSTRACT

Provided is a medical instrument which has improved operability of an insertion portion and can guide a distal end of the insertion portion to an intended position. The medical instrument includes: an insertion portion (10) which is inserted into a body cavity; a rotor (11) which is provided in an outer circumferential surface of the insertion portion (10) and has its rotational axis arranged in a direction along an axis of the insertion portion (10); and a rotary drive unit which rotates the rotor (11) around the rotational axis.

21 Claims, 39 Drawing Sheets

(56) References Cited

U.S. PATENT DOCUMENTS

| | | | |
|---|---|---|---|
| 6,183,487 B1 | 2/2001 | Barry et al. | |
| 6,258,109 B1 | 7/2001 | Barry et al. | |
| 6,270,509 B1 | 8/2001 | Barry et al. | |
| 6,328,750 B1 | 12/2001 | Berry et al. | |
| 6,482,216 B1 | 11/2002 | Hiblar et al. | |
| 2002/0156347 A1* | 10/2002 | Kim | A61B 1/00156 600/160 |
| 2008/0255423 A1* | 10/2008 | Kondo | A61B 17/3478 600/146 |
| 2009/0069821 A1* | 3/2009 | Farritor | A61B 1/00158 606/130 |
| 2009/0247821 A1* | 10/2009 | Rogers | A61B 1/00098 600/104 |
| 2013/0035552 A1* | 2/2013 | Moriyama | 600/149 |

FOREIGN PATENT DOCUMENTS

| | | |
|---|---|---|
| JP | 2000-23908 A | 1/2000 |
| JP | 2000-271064 A | 10/2000 |
| JP | 2001-510383 A | 7/2001 |
| JP | 2005-287593 A | 10/2005 |
| JP | 2005-288035 A | 10/2005 |
| JP | 2005-319121 A | 11/2005 |
| JP | 2005-328998 A | 12/2005 |
| JP | 2005-329079 A | 12/2005 |
| JP | 2007-185394 A | 7/2007 |
| JP | 2009-125392 A | 6/2009 |
| JP | 2009-254554 A | 11/2009 |
| JP | 2011-520563 A | 7/2011 |
| WO | WO 2008/105393 A1 | 9/2008 |
| WO | 2009/143077 A9 | 11/2009 |

\* cited by examiner

CROSS-SECTIONAL VIEW A

CROSS-SECTIONAL VIEW B

CROSS-SECTIONAL VIEW C

MEDICAL INSTRUMENT

CROSS-REFERENCE TO RELATED APPLICATIONS

This application is based on Japanese Patent Application No. 2011-160494, the contents of which are incorporated herein by reference.

TECHNICAL FIELD

The present invention relates to a medical instrument which includes an insertion portion to be inserted into a body cavity.

BACKGROUND ART

Conventionally, in the field of medical instruments such as endoscopes, a medical instrument is known which includes an insertion portion to be inserted into a body cavity in order to observe or treat a diseased part inside the body cavity (e.g., see PTL 1 and PTL 2).

This medical instrument has a curving portion through which a curvature of the insertion portion is changed by pulling a wire cable disposed inside the insertion portion. Specifically, the curving portion has a structure such that pulling the wire cable causes the side of the curving portion pulled by the wire to be drawn toward the user's hand, which curves the curving portion.

CITATION LIST

Patent Literature

{PTL 1}
Japanese Unexamined Patent Application, Publication No. 2000-23908
{PTL 2}
Japanese Unexamined Patent Application, Publication No. 2005-329079

SUMMARY OF INVENTION

Technical Problem

With the medical instruments disclosed in PTL 1 or PTL 2, the direction of the distal end of the insertion portion relative to an observation position or a treatment position is changed by curving the curving portion so as to bow the distal end of the insertion portion. However, in a space such as a pericardial cavity where pressure is applied from both directions, from the heart side as well as from a pericardium side, it is difficult to guide the distal end of the insertion portion to an intended position simply by changing the direction of the distal end, which can be inconvenient.

The present invention has been made in view of the above situation, and an object thereof is to provide a medical instrument which has improved operability of the insertion portion and can guide the distal end of the insertion portion to an intended position.

Solution to Problem

In order to achieve the above object, the present invention provides the following solutions.

The present invention has adopted a medical instrument which includes: an insertion portion which is inserted into a body cavity; a rotor which is provided in an outer circumferential surface of the insertion portion and has its rotational axis arranged in a direction along an axis of the insertion portion; and a rotary drive unit which rotates the rotor around the rotational axis.

In the above invention, the rotor may be provided so as to be partially exposed in the outer circumferential surface of the insertion portion.

The above invention may include a curving portion which is provided in the insertion portion and curves the insertion portion.

In the configuration including the curving portion, a rigid portion may be provided further on a distal end side than the curving portion of the insertion portion, and the rotor may be provided in the rigid portion.

In the configuration including the rigid portion, a plurality of the rotors may be provided in the rigid portion of the insertion portion.

In the configuration including the plurality of rotors, the plurality of rotors may be arranged symmetrically with respect to the axis of the insertion portion.

In the above invention, a flexible portion may be provided further on a proximal end side than the curving portion of the insertion portion, and the rotor may be provided in the flexible portion.

Alternatively, the rotor may be provided only in the flexible portion without being provided in the rigid portion.

In the above invention, the rotor may protrude outward in a radial direction from the outer circumferential surface of the insertion portion.

The above configuration may include an inclined plane formed between the outer circumferential surface of the insertion portion and an outer circumferential surface of the rotor.

In the above invention, the rotational axis of the rotor and a central axis of the insertion portion may be arranged at positions eccentric to each other.

In the above invention, an exposed portion of the rotor may occupy approximately a half of the outer circumference of the insertion portion in a circumferential direction of the insertion portion.

In the above invention, the rotor may be constituted of a rigid cylindrical member to which the drive force from the rotary drive unit is transmitted, and a flexible elastic member which is provided outside the cylindrical member.

In the above invention, the rotor may be a crawler belt constituted of a flexible elastic member.

The above invention may include projections on the outer circumferential surface of the rotor.

In the configuration including the projections, the projections may be formed in the direction along the axis of the insertion portion.

The above invention may include a wire which is arranged inside the insertion portion in the axial direction and is connected to the rotational axis of the rotor.

The above configuration including the wire may further include a rotary operation part which is arranged on the proximal end side of the insertion portion and rotates the wire around the axis.

In the above invention, the insertion portion may have a flat shape, and the rotor may be exposed in a short axis direction of a transverse section of the insertion portion.

In the above invention, the rotor may expand outward in the radial direction of the insertion portion.

In the above invention, the rotary drive unit may include a plurality of gears having different numbers of teeth which The above invention may include an imaging unit which is provided at the distal end of the insertion portion and obtains an image of the inside of the body cavity.

The configuration including the imaging unit may further include a display unit which displays the image obtained by the imaging unit, and the display unit may display a mark which indicates a position of the rotor in the image obtained by the imaging unit.

DESCRIPTION OF EMBODIMENTS

{First Embodiment}

Hereinafter, an endoscope according to a first embodiment of the present invention will be described with reference to the drawings.

Figure 1:
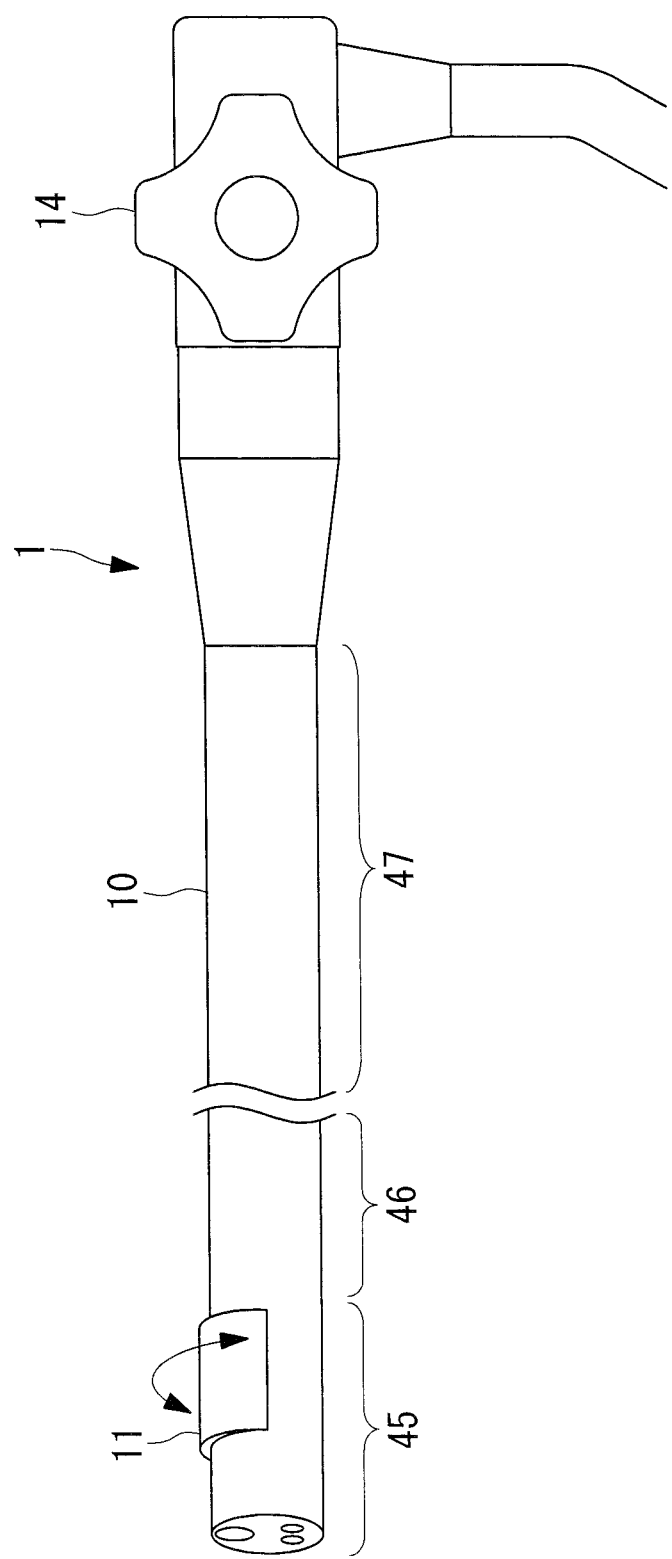
FIG. 1 is a schematic configuration view of an endoscope according to a first embodiment of the present invention.

As shown in FIG. 1, an endoscope 1 according to the present embodiment includes: a long, thin insertion portion 10 which is inserted into a body cavity; a rotary operation part 14 which operates the motion of the insertion portion 10; and a display unit (not shown) which displays an image obtained by the insertion portion 10.

The insertion portion 10 is formed of the following, continuously integrated from a distal end side: a rigid portion 45 constituted of a rigid material; a curving portion 46 which is three-dimensionally curved by a user's operation of a curving operation part to be described later; and an elongated flexible portion 47 constituted of a flexible material. Furthermore, a proximal end of the flexible portion 47 is connected to the rotary operation part 14, such as a dial.

Figure 4:
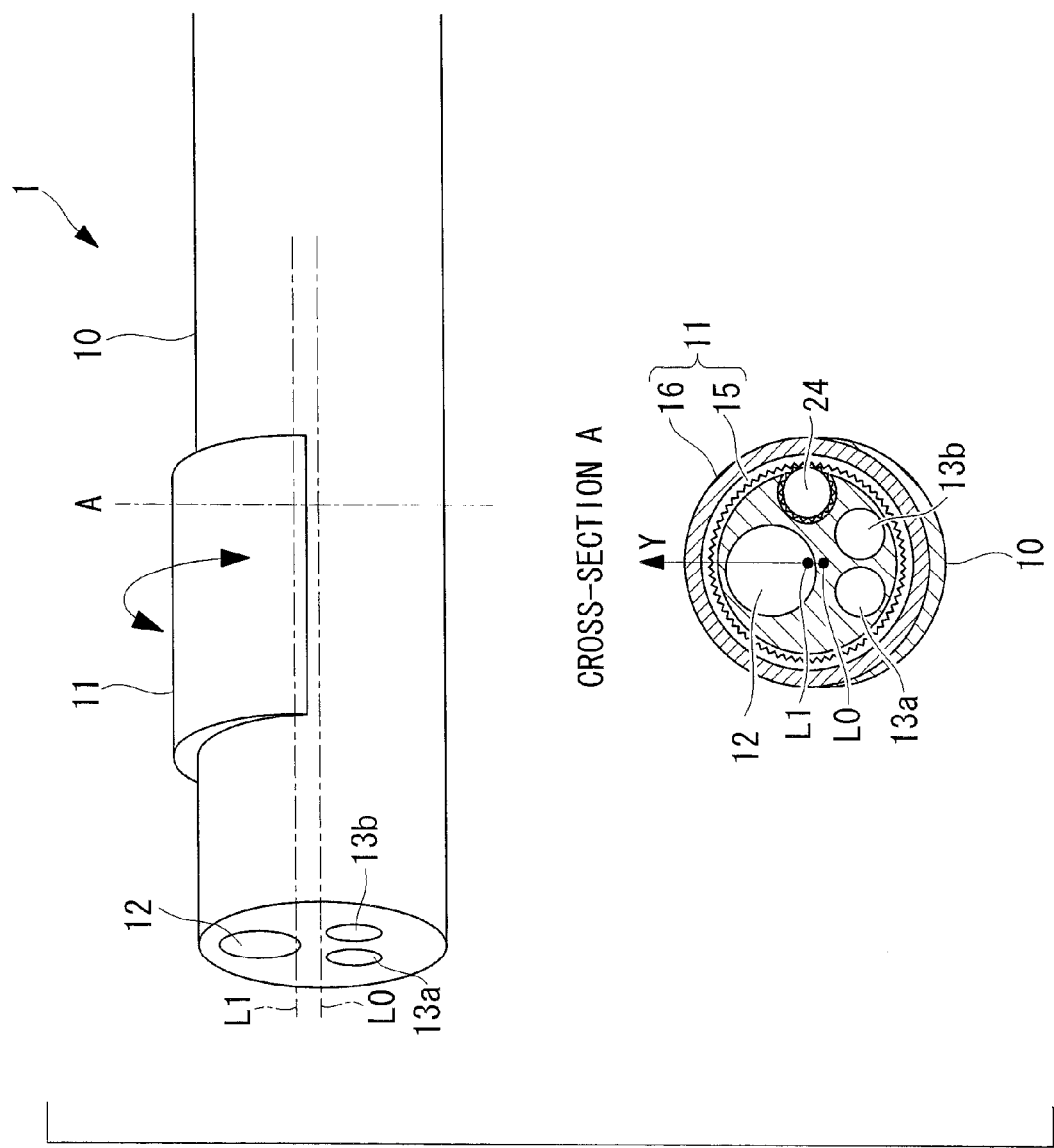
FIG. 4 is a partially enlarged view of the endoscope of FIG. 1.

A rotor 11 is provided in an outer circumferential surface of the rigid portion 45 of the insertion portion 10 so as to be partially exposed, and has its rotational axis (reference sign L1 in FIG. 4) arranged in a direction along an axis of the insertion portion 10 (reference sign L0 in FIG. 4).

Figure 2:
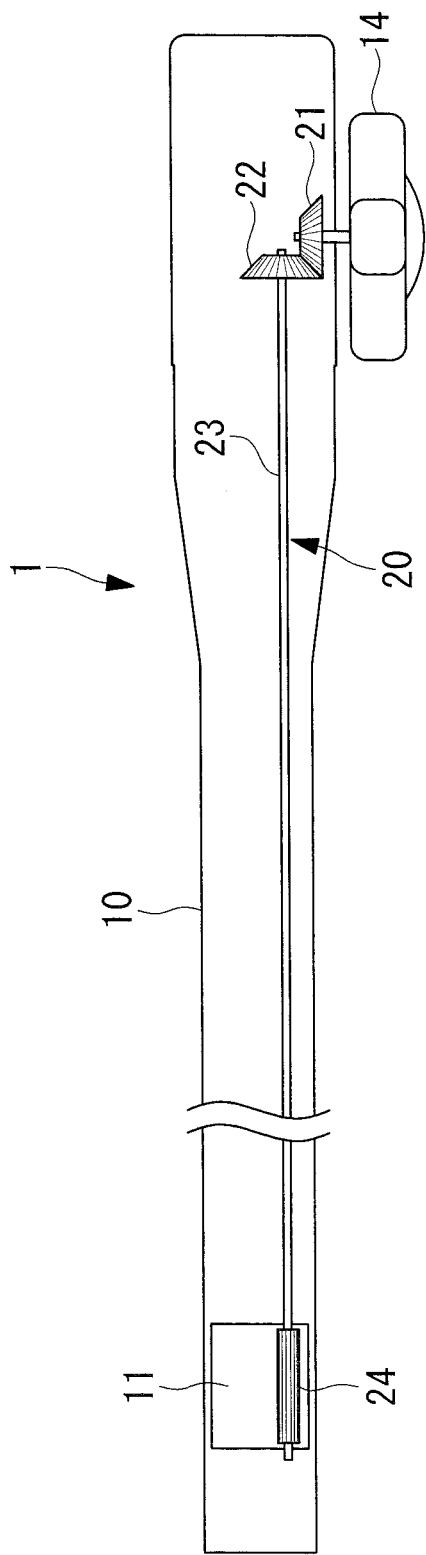
FIG. 2 is a longitudinal cross-sectional view of the endoscope of FIG. 1.

As shown in FIG. 2, the insertion portion 10 is provided with a rotary drive unit 20 which rotates the rotor 11 around the rotational axis.

As shown in FIG. 4, a distal end surface of the insertion portion 10 is provided with: a light guide 13a which guides illumination light from a lighting device (not shown) and irradiates an observation region with the illumination light; a camera (imaging unit) 12, such as a CCD, which obtains an image of the observation region irradiated by the light guide 13a; and a forceps channel 13b through which a treatment tool such as forceps is inserted.

This configuration makes it possible to guide the distal end of the insertion portion to an intended position, and obtain an image of the inside of the body cavity by the imaging unit to perform an endoscopic observation of a desired observation object.

The light guide 13a is inserted in an axial direction of the insertion portion 10, and is connected to the lighting device (not shown) arranged on the proximal end side. The forceps channel 13b is formed in the axial direction of the insertion portion 10, and leads out the treatment tool introduced from an introduction port (not shown) arranged on the proximal end side. A signal line from the camera 12 is inserted in the axial direction of the insertion portion 10 and connected to a control unit (not shown) and the display unit (not shown) arranged on the proximal end side.

As shown in FIG. 2, the rotary drive unit 20 includes: a gear 21 connected to a rotational axis of the rotary operation part 14; a gear 22 meshing with the gear 21; a drive transmission wire 23 connected to a rotational axis of the gear 22; and a drive transmission gear 24 arranged on the distal end side of the drive transmission wire 23.

The gear 21 has its rotational axis arranged in the direction perpendicular to the axis of the insertion portion 10.

The gear 22 has its rotational axis arranged in the direction along the axis of the insertion portion 10. The gear 21 and the gear 22 have meshing surfaces formed at an angle of 45° to the respective rotational axes.

In other words, the gear 21 and the gear 22 have their rotational axes arranged in the directions perpendicular to each other, and are meshed with each other. With this configuration, the rotation of the gear 21 around the rotational axis (the rotational axis perpendicular to the axis of the insertion portion 10) can be converted into the rotation of the gear 22 around the rotational axis (the rotational axis along the axis of the insertion portion 10).

The drive transmission wire 23 is arranged in the direction along the axis of the insertion portion 10, and transmits the rotation of the gear 22 connected to the proximal end side to the drive transmission gear 24 connected to the distal end side.

As shown in FIG. 4, the outer circumferential surface of the drive transmission gear 24 meshes with the inner circumferential surface of a cylindrical member 15 of the rotor 11.

Figure 3:
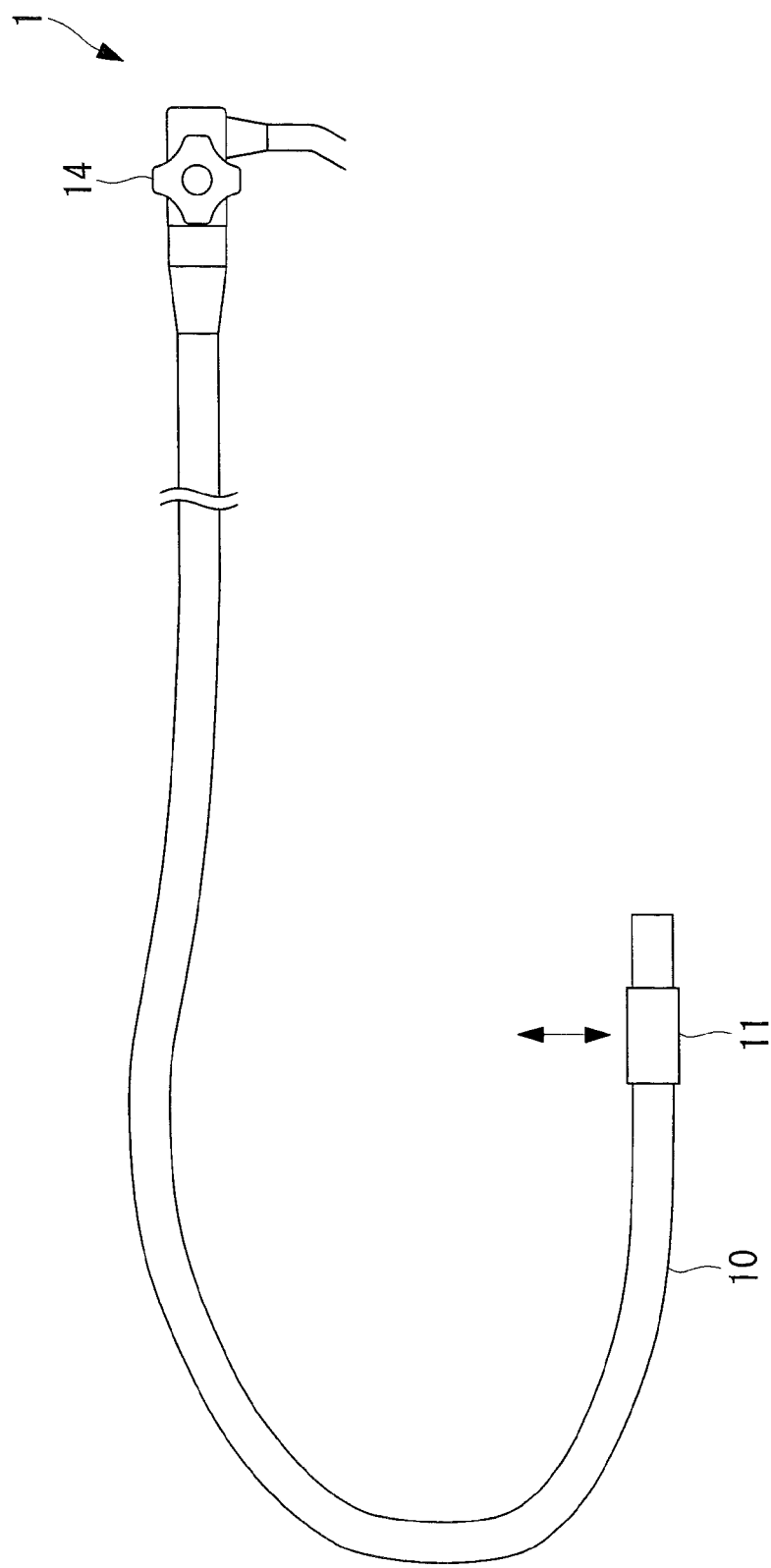
FIG. 3 is a view for explaining a motion of the endoscope of FIG. 1.

According to the rotary drive unit 20 having the above configuration, rotating the rotary operation part 14 causes its drive force to be transmitted from the gear 21 to the gear 22, being converted into the rotation around the rotational axis along the axis of the insertion portion 10. This rotation is transmitted by the drive transmission wire 23 to the drive transmission gear 24, causing the cylindrical member 15 of the rotor 11 to rotate. Thus, the drive force is applied to an inner wall of a body cavity in contact with the rotor 11, allowing the insertion portion 10, as shown in FIG. 3, to be moved in the direction along the surface of the inner wall of the body cavity (the direction perpendicular to the axis of the insertion portion 10).

This configuration allows the drive force from the rotary drive unit to be reliably transmitted through the wire to the rotor. Further, this configuration allows the wire to be rotated around the axis by operation of the rotary operation part, such as a dial, arranged on the proximal end side of the insertion portion, so as to rotate the rotor connected to the wire around the axis. Thus, the insertion portion can be moved by such a very simple configuration in the direction perpendicular to the axis, and as the intuitive operation is possible, operational errors can be prevented.

As shown in FIG. 4, the rotor 11 is constituted of the rigid cylindrical member 15 to which the drive force from the rotary drive unit 20 is transmitted, and a flexible elastic member 16 which is provided outside the cylindrical member 15. The inner circumferential surface of the cylindrical member 15 is formed with teeth which mesh with the drive transmission gear 24.

This configuration makes it possible to reliably receive the drive force from the rotary drive unit 20 by the rigid cylindrical member 15, as well as to transmit the drive force by the elastic member 16 provided outside, without causing any damage to the inner wall of the body cavity. Thus, the insertion portion 10 can be moved in the direction along the surface of the inner wall of the body cavity (the direction perpendicular to the axis of the insertion portion 10) so as to guide the distal end of the insertion portion 10 to an intended position.

Here, the rotor 11 is provided in the rigid portion 45 of the insertion portion 10.

This configuration can reduce the influence of an external force acting on the distal end of the insertion portion 10, allowing the distal end of the insertion portion 10 to be more reliably guided to an intended position. Furthermore, by providing the rotor 11 in the rigid portion 45 on the distal end side of the insertion portion 10, the position of the distal end of the insertion portion 10 can be finely adjusted.

As shown in FIG. 4, the rotor 11 protrudes outward in the radial direction (the direction indicated by the arrow Y in FIG. 4) from the outer circumferential surface of the insertion portion 10.

With this configuration, the rotor 11 can be more reliably brought into contact with the inner wall of the body cavity, allowing the drive force of the rotor 11 to be efficiently transmitted to the inner wall of the body cavity, so as to move the insertion portion 10 in the direction perpendicular to the axis.

More specifically, the rotational axis of the rotor 11 and a central axis of the insertion portion 10 are arranged at positions eccentric to each other. Specifically, as shown in FIG. 4, the central axis of the insertion portion 10 indicated by the reference sign L0 and the rotational axis of the rotor 11 indicated by the reference sign L1 are arranged at the positions eccentric to each other.

This configuration can make it easy to protrude the rotor 11 only partially outward in the radial direction from the outer circumferential surface of the insertion portion 10, thereby allowing the drive force of the rotor 11 to be efficiently transmitted to the inner wall of the body cavity, so as to move the insertion portion 10 in the direction perpendicular to the axis.

Furthermore, an exposed portion of the rotor 11 occupies approximately a half of the outer circumference of the insertion portion 10 in a circumferential direction of the insertion portion 10.

If the exposed portion of the rotor 11 occupies a half or more of the outer circumference of the insertion portion 10, the rotor 11 constantly comes into contact with both of opposite inner walls of the body cavity, such as a pericardium and a heart, at the same time. This state is undesirable, as the drive force of the rotor 11 cannot be efficiently used for moving the insertion portion 10. On the other hand, a smaller contact area between the rotor 11 and the inner wall of the body cavity results in a smaller drive force to be transmitted to the inner wall of the body cavity. Therefore, with the exposed portion of the rotor 11 occupying about a half of the outer circumference of the insertion portion 10, the drive force of the rotor 11 can be efficiently used for moving the insertion portion 10.

The curving operation part (not shown) which operates the curving motion of the curving portion 46, such as an operation lever, may be provided at the proximal end of the flexible portion 47. This curving operation part has a configuration such that a user's operation of the operation lever causes a curving operation wire (not shown) inserted inside the insertion portion 10 to be pulled in a longitudinal direction, which causes the curving portion 46 to make a curving motion in three-dimensional directions. More specifically, the curving operation part curves the curving portion 46 in a direction, toward which the operation lever, for example, is inclined by the user, at an angle according to the inclined angle of the operation lever.

This configuration not only allows the insertion portion 10 to be moved by the rotor 11 in the direction perpendicular to the axis of the insertion portion 10, but also allows the insertion portion 10 to be moved by curving the curving portion 46. Thus, the moving range of the insertion portion 10 can be expanded and the operability of the insertion portion 10 can be improved.

Figure 6:
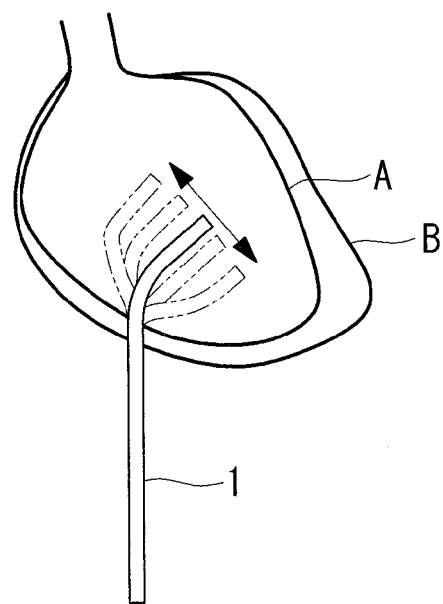
FIG. 6 is a view showing a state where the endoscope of FIG. 1 makes a parallel movement inside the pericardial cavity.
Figure 7:
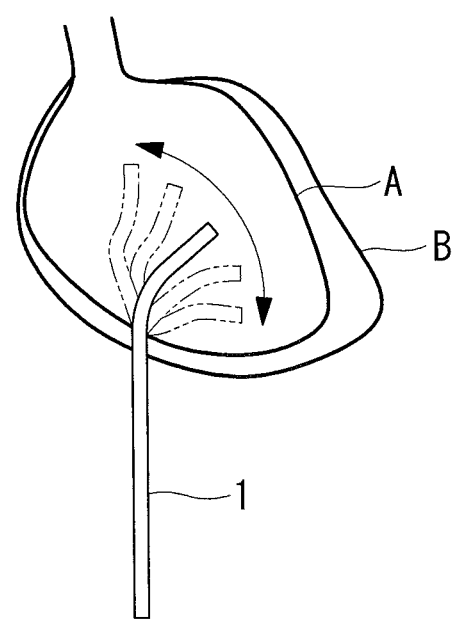
FIG. 7 is a view showing a state where the endoscope of FIG. 1 makes a combination of the curving motion and the parallel movement inside the pericardial cavity.

In the following, the working of the insertion portion 10 of the endoscope 1 having the above configuration will be described. Here, as shown in FIGS. 5 to 7, the insertion portion 10 of the endoscope 1 according to the present embodiment will be described in terms of its motion when inserted into a pericardial cavity between a heart A and a pericardium B.

When the insertion portion 10 of the endoscope 1 according to the present embodiment is inserted into the pericardial cavity, the rotor 11, which is provided in the outer circumferential surface of the insertion portion 10 so as to be partially exposed, comes into contact either with the heart A or with the pericardium B. In this state, actuating the rotary drive unit 20 causes the rotor 11 to rotate around its rotational axis arranged in the direction along the axis of the insertion portion 10. Thus, the drive force is transmitted either to the heart A or to the pericardium B, allowing the insertion portion 10 to be moved in the direction along the surface of the heart A or the pericardium B (the direction perpendicular to the axis of the insertion portion 10).

As a comparative example here, the motion in a case where the endoscope 1 makes only the curving motion, as with the conventional endoscopes, will be described below.

Figure 5:
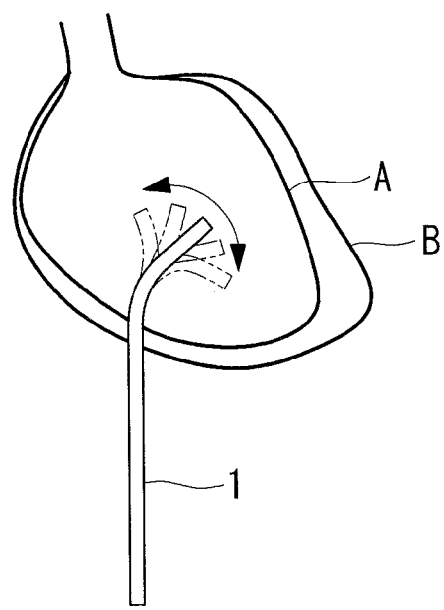
FIG. 5 is a view showing a state where the endoscope of FIG. 1 makes a curving motion inside a pericardial cavity.

In this case, as shown in FIG. 5, the direction of the distal end of the insertion portion relative to an observation position or a treatment position is changed by curving the curving portion so as to bow the distal end of the insertion portion. However, in a space such as a pericardial cavity where pressure is applied from both directions, from the heart A side as well as from the pericardium B side, it is difficult to guide the distal end of the insertion portion to an intended position simply by changing the direction of the distal end.

In this case, as shown in FIG. 6, the endoscope 1 according to the present embodiment can move the insertion portion 10 in the direction perpendicular to the axis of the insertion portion 10. Thus, even in a space such as a pericardial cavity where pressure is applied from both directions, from the heart A side as well as from the pericardium B side, the distal end of the insertion portion 10 can be guided to an intended position.

In the endoscope 1 according to the present embodiment, since the rotor 11 is only partially exposed in the outer circumferential surface of the insertion portion 10, the rotor can be prevented from coming into contact with both the heart A and the pericardium B and transmitting the drive force in an opposite direction. Thus, the insertion portion 10 can be efficiently moved in the direction along the surface of the heart A or the pericardium B (the direction perpendicular to the axis of the insertion portion 10).

As shown in FIG. 7, the endoscope 1 according to the present embodiment may make a combination of the motion of moving in the direction perpendicular to the axis of the insertion portion 10 by the rotor 11 and the curving motion by the curving portion 46.

This not only allows the insertion portion 10 to be moved by the rotor 11 in the direction perpendicular to the axis, but also allows the insertion portion 10 to be moved by curving the curving portion 46. Thus, the moving range of the insertion portion 10 can be expanded, as well as the operability of the insertion portion 10 can be improved.

(First Modified Example)

Figure 8:
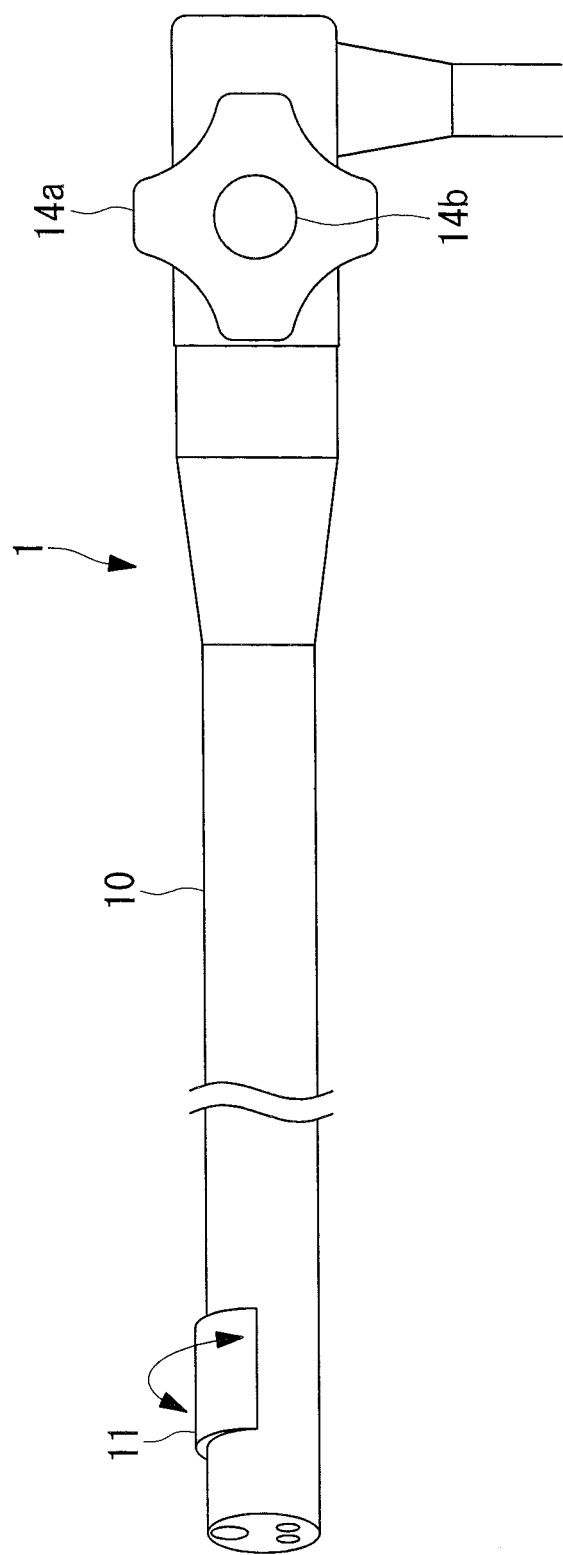
FIG. 8 is a schematic configuration view of an endoscope according to a first modified example of FIG. 1.
Figure 9:
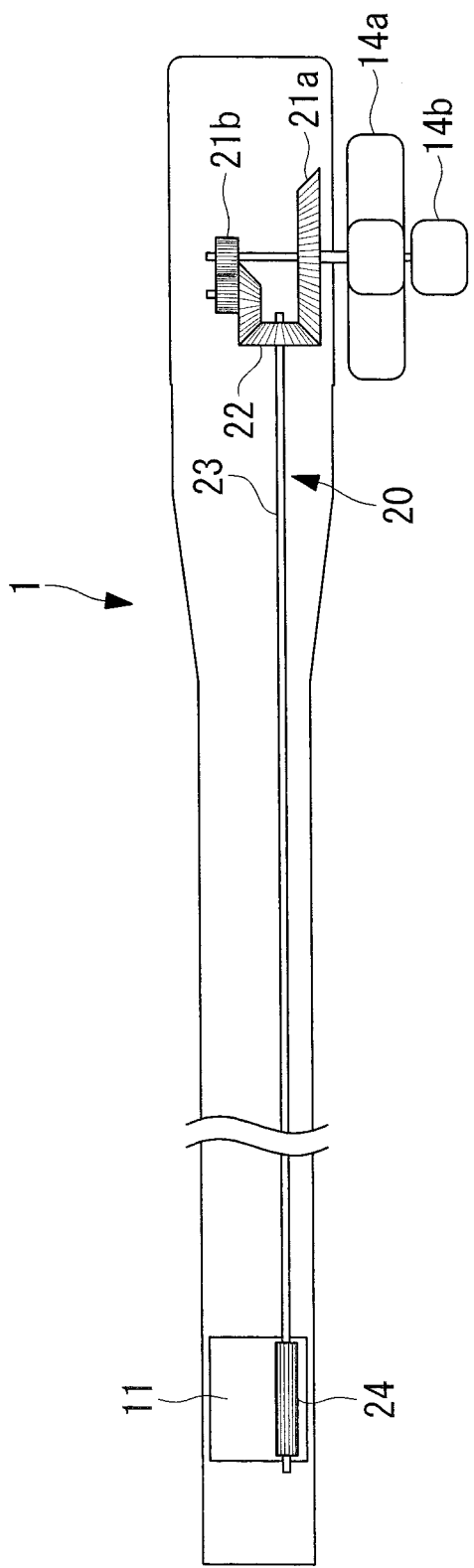
FIG. 9 is a longitudinal cross-sectional view of the endoscope of FIG. 8.

As shown in FIGS. 8 and 9, as a first modified example of the endoscope 1 according to the present embodiment, the rotary drive unit 20 may include a plurality of gears having different numbers of teeth which transmit the drive force to the rotor 11, and a gear switching mechanism (not shown) which switches between these gears.

As shown in FIG. 9, the rotary drive unit 20 in the endoscope 1 according to this modified example includes: a gear 21a having a larger number of teeth and connected to the rotational axis of a rotary operation part 14a; a gear 21b having a smaller number of teeth and connected to the rotational axis of a rotary operation part 14b; the gear 22 meshing with these gears 21a and 21b; the drive transmission wire 23 connected to the rotational axis of the gear 22; and the drive transmission gear 24 arranged at the distal end side of the drive transmission wire 23.

This configuration allows the insertion portion 10 to be moved by switching between these gears 21a and 21b having different numbers of teeth according to the purpose. Specifically, by operating the rotary operation part 14a so as to transmit the drive force to the rotor 11 through the gear 21a having a larger number of teeth, the insertion portion 10 can be quickly moved in the direction perpendicular to the axis. Furthermore, by operating the rotary operation part 14b so as to transmit the drive force to the rotor 11 through the gear 21b having a smaller number of teeth, the insertion portion 10 can be precisely moved in the direction perpendicular to the axis.

The gear 21b is constituted of two trains of gears mounted in parallel, with the rotational direction having being reversed once. Accordingly, when rotated in the same direction, the rotary operation part 14a and the rotary operation part 14b cause the drive transmission wire 23 to rotate in the same direction. Thus, whether the rotary operation part 14a is operated or the rotary operation part 14b is operated when driving the rotor 11, the rotational direction of the operation part and the moving direction are the same, which prevents confusion in the operation.

(Second Modified Example)

Figure 10:
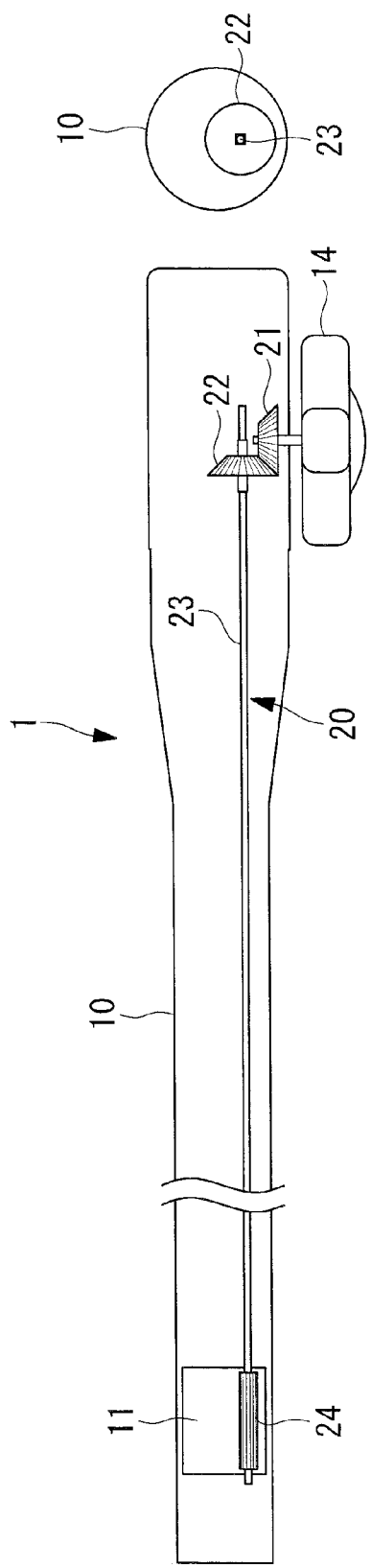
FIG. 10 is a longitudinal cross-sectional view of an endoscope according to a second modified example of FIG. 1.

As shown in FIG. 10, as a second modified example of the endoscope 1 according to the present embodiment, a tension reducing mechanism for the drive transmission wire 23 may be provided.

In the endoscope 1 according to this modified example, connecting portions of the drive transmission wire 23 and the gear 22 are not joined, but instead, a square hole is opened in the gear 22. On the other hand, the transverse section of a portion of the drive transmission wire 23 which engages with the gear 22 is formed into a slightly smaller square than the hole in the gear 22.

Although the rotation of the gear 22 is transmitted by the square hole of the gear 22 and the square shaft of the drive transmission wire 23 engaging with each other, they are freely movable in the axial direction. This allows the drive transmission wire 23 to shift in the axial direction, thereby reducing the tension applied to the drive transmission wire 23 so as to efficiently transmit the drive force to the rotor 11.

Although in this modified example, the example has been described where the hole in the gear 22 and the transverse section of the drive transmission wire 23 are each formed into a square shape, they are not limited to this shape; as long as the gear 22 and the drive transmission wire 23 can engage with each other around the axis, other polygonal shapes or an oblong shape, or a circular shape with a projection or a notch may be adopted.

{Second Embodiment}

Next, an endoscope according to a second embodiment of the present invention will be described with reference to the drawings. In the following, endoscopes of various embodiments will be described mainly in terms of differences from previously described embodiments, while similarities thereto will be denoted by the same reference signs and not described.

Figure 11:
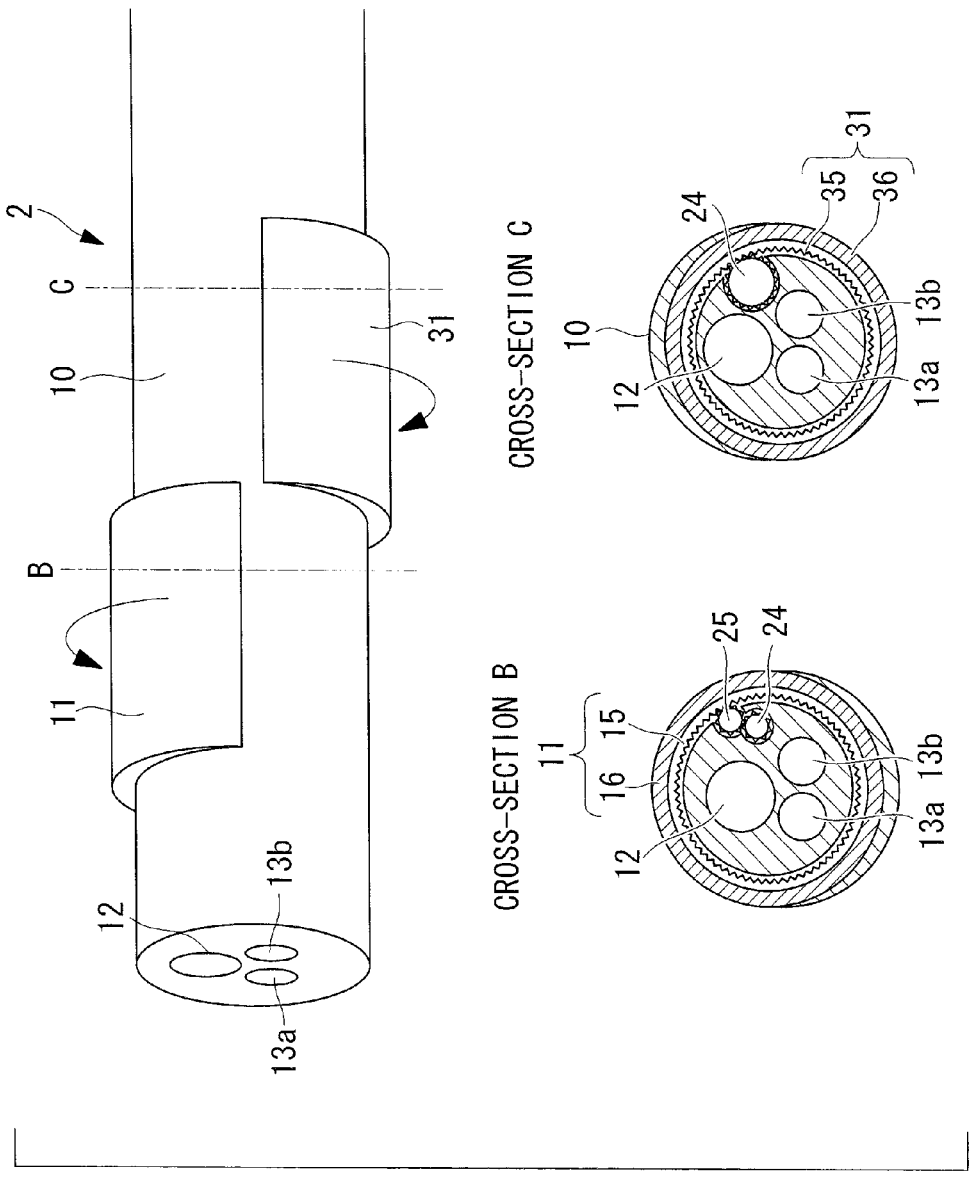
FIG. 11 is a partially enlarged view of an endoscope according to a second embodiment of the present invention.

As shown in FIG. 11, an endoscope 2 according to the present embodiment is provided with two rotors in the rigid portion 45 of the insertion portion 10, and these rotors are arranged symmetrically with respect to the axis of the insertion portion 10.

Specifically, the rotor 11 and a rotor 31 having their rotational axes arranged in the direction along the axis of the insertion portion 10 are provided in the outer circumferential surface of the rigid portion 45 of the insertion portion 10 at positions symmetrical with respect to the axis of the insertion portion 10.

This configuration can reliably bring any one of the rotors into contact with an inner wall of a body cavity, allowing the insertion portion to be moved in the direction perpendicular to the axis.

As shown in FIG. 11, the rotor 31 has a configuration similar to that of the rotor 11, and is constituted of a rigid cylindrical member 35, to which the drive force from the rotary drive unit 20 is transmitted, and a flexible elastic member 36, which is provided outside the cylindrical member 35. The inner circumferential surface of the cylindrical member 35 is formed with teeth which mesh with the drive transmission gear 24. As shown in the cross-section B of FIG. 11, a drive transmission gear 25 meshing with the drive transmission gear 24 is meshed with the cylindrical member 15 of the rotor 11.

Due to this configuration, rotating the rotary operation part 14 causes its drive force to be transmitted by the drive transmission wire 23 to the drive transmission gear 24, causing the cylindrical member 35 of the rotor 31 to rotate. Furthermore, this drive force is transmitted from the drive transmission gear 24 to the drive transmission gear 25, causing the cylindrical member 15 of the rotor 11 to rotate in an opposite direction to the cylindrical member 35 of the rotor 31.

According to the endoscope 2 of the present embodiment, due to the above configuration, the rotors 11 and 31 can be brought into contact with both the heart A and the pericardium B when the insertion portion 10 is inserted into a body cavity such as a pericardial cavity. Thus, the drive force of the rotors 11 and 31 can be applied to both the heart A and the pericardium B, allowing the insertion portion 10 to be more reliably guided to an intended position.

In addition, since the rotor 11 and the rotor 31 are rotated in the opposite directions, rotation of the insertion portion 10 itself can be prevented, which allows the insertion portion 10 to be reliably moved in the direction along the surface of the heart A or the pericardium B (the direction perpendicular to the axis of the insertion portion 10).

(Modified Example)

Figure 12:
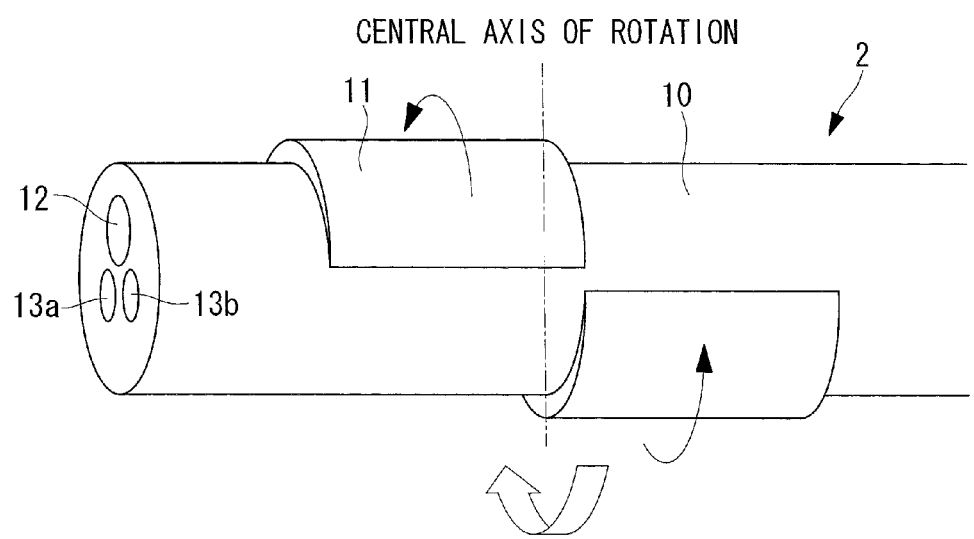
FIG. 12 is a partially enlarged view of an endoscope according to a modified example of FIG. 11.

As shown in FIG. 12, as a modified example of the endoscope 2 according to the present embodiment, the rotor 11 and the rotor 31 may be rotated in the same direction.

Figure 13:
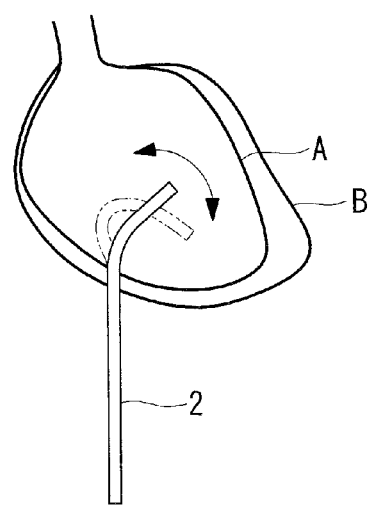
FIG. 13 is a view showing a state where the endoscope of FIG. 12 makes a motion inside the pericardial cavity.

This makes it possible to turn the endoscope 2 in a smaller turning radius by applying the force in the opposite directions with the boundary between the rotor 11 and the rotor 31. Accordingly, as shown in FIG. 13, fine operation of the endoscope 2 can be performed even in a narrow space such as a pericardial cavity.

{Third Embodiment}

Next, an endoscope according to a third embodiment of the present invention will be described with reference to the drawings.

Figure 14:
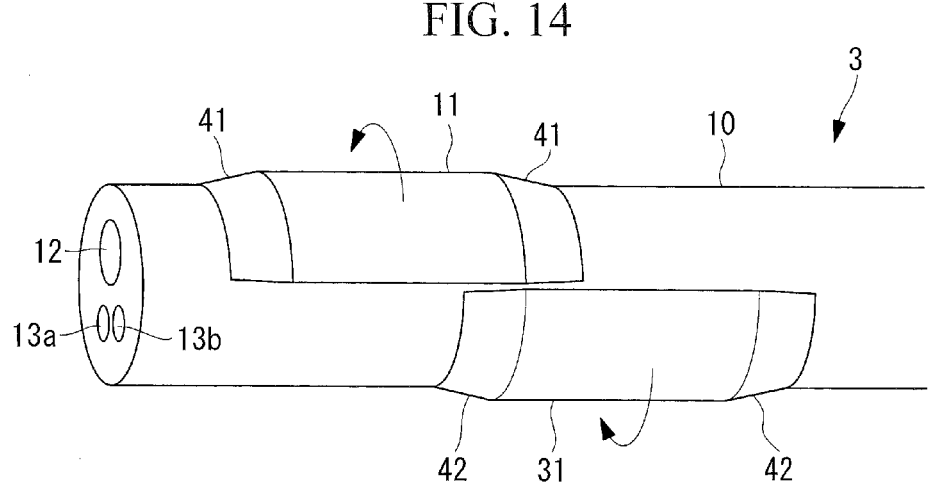
FIG. 14 is a partially enlarged view of an endoscope according to a third embodiment of the present invention.

As shown in FIG. 14, an endoscope 3 according to the present embodiment is provided with tapered portions (inclined planes) 41 and 42 in a front-rear direction (the direction along the axis of the insertion portion 10) of the rotor 11 and the rotor 31, respectively.

The rotors 11 and 31 protrude outward in the radial direction from the outer circumferential surface of the insertion portion 10.

The tapered portions 41 and 42 are inclined planes formed between the outer circumferential surface of the insertion portion 10 and the respective outer circumferential surfaces of the rotors 11 and 31.

Here, if the rotors 11 and 31 protrude outward in the radial direction from the outer circumferential surface of the insertion portion 10, these rotors 11 and 31 become resistance in moving the insertion portion 10 in the axial direction, which can hinder the smooth movement. In addition, the rotors 11 and 31 can get caught on the inner wall of the body cavity.

In contrast, according to the endoscope 3 of the present embodiment, since the rotor 11 and the rotor 31 are respectively provided with the tapered portions 41 and 42 in the front-rear direction, the resistance in moving the insertion portion 10 in the axial direction can be reduced, as well as the rotors 11 and 31 can be prevented from getting caught on the inner wall of the body cavity. Thus, the insertion portion can be moved more smoothly in the axial direction.

(First Modified Example)

Figure 15:
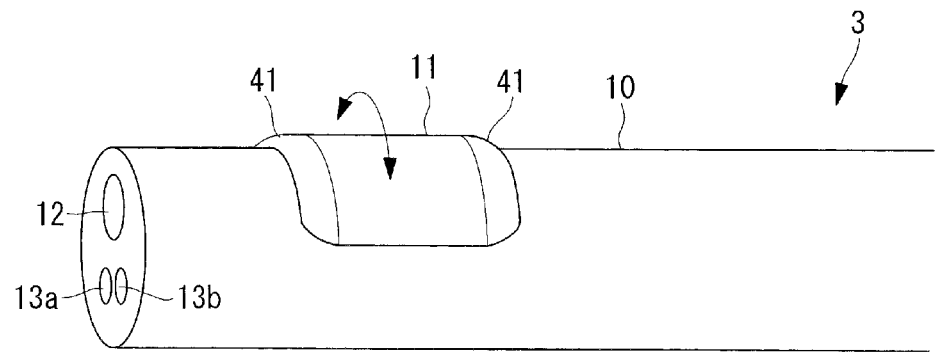
FIG. 15 is a partially enlarged view of an endoscope according to a first modified example of FIG. 14.

As shown in FIG. 15, as a modified example of the endoscope 3 according to the present embodiment, the rotor 11 itself may be provided with the tapered portions 41, which approach the outer circumferential surface of the insertion portion 10 from the outer circumferential surface of the rotor 11 (the surface protruding outward in the radial direction), in the front-rear direction of the rotor 11 (the direction along the axis of the insertion portion 10).

(Second Modified Example)

Figure 16:
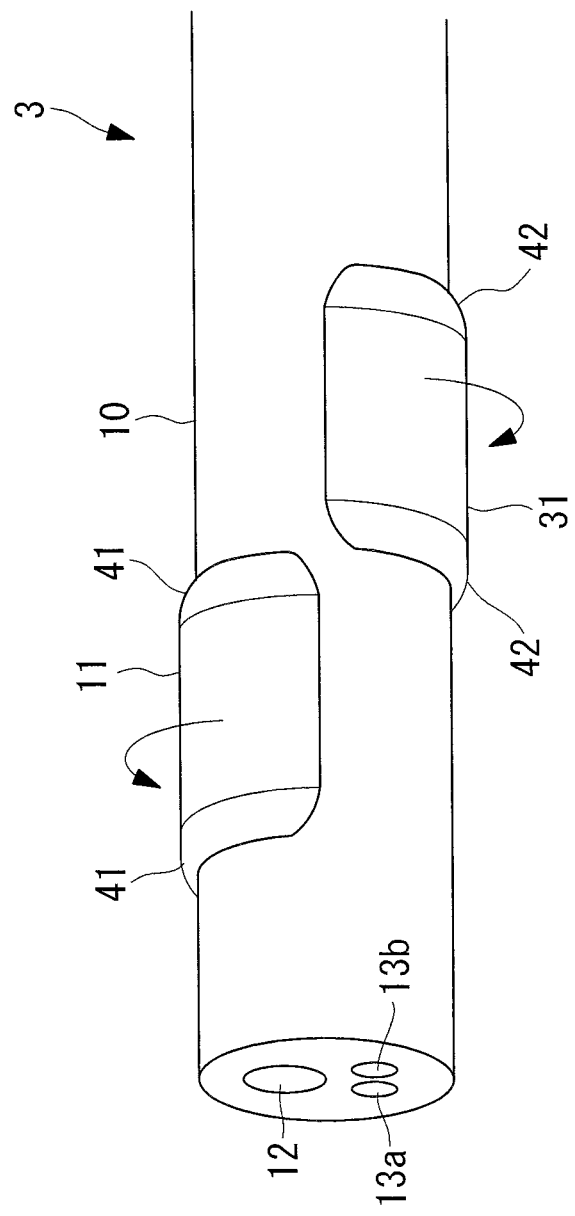
FIG. 16 is a partially enlarged view of an endoscope according to a second modified example of FIG. 14.

As shown in FIG. 16, as a second modified example of the endoscope 3 according to the present embodiment, the rotors 11 and 31 themselves may be respectively provided with the tapered portions 41 and 42 which approach the outer circumferential surface of the insertion portion 10 from the outer circumferential surfaces of the rotors 11 and 31 (the surfaces protruding outward in the radial direction), in the front-rear direction of the rotors 11 and 31 (the direction along the axis of the insertion portion 10).

{Fourth Embodiment}

Next, an endoscope according to a fourth embodiment of the present invention will be described with reference to the drawings.

Figure 17:
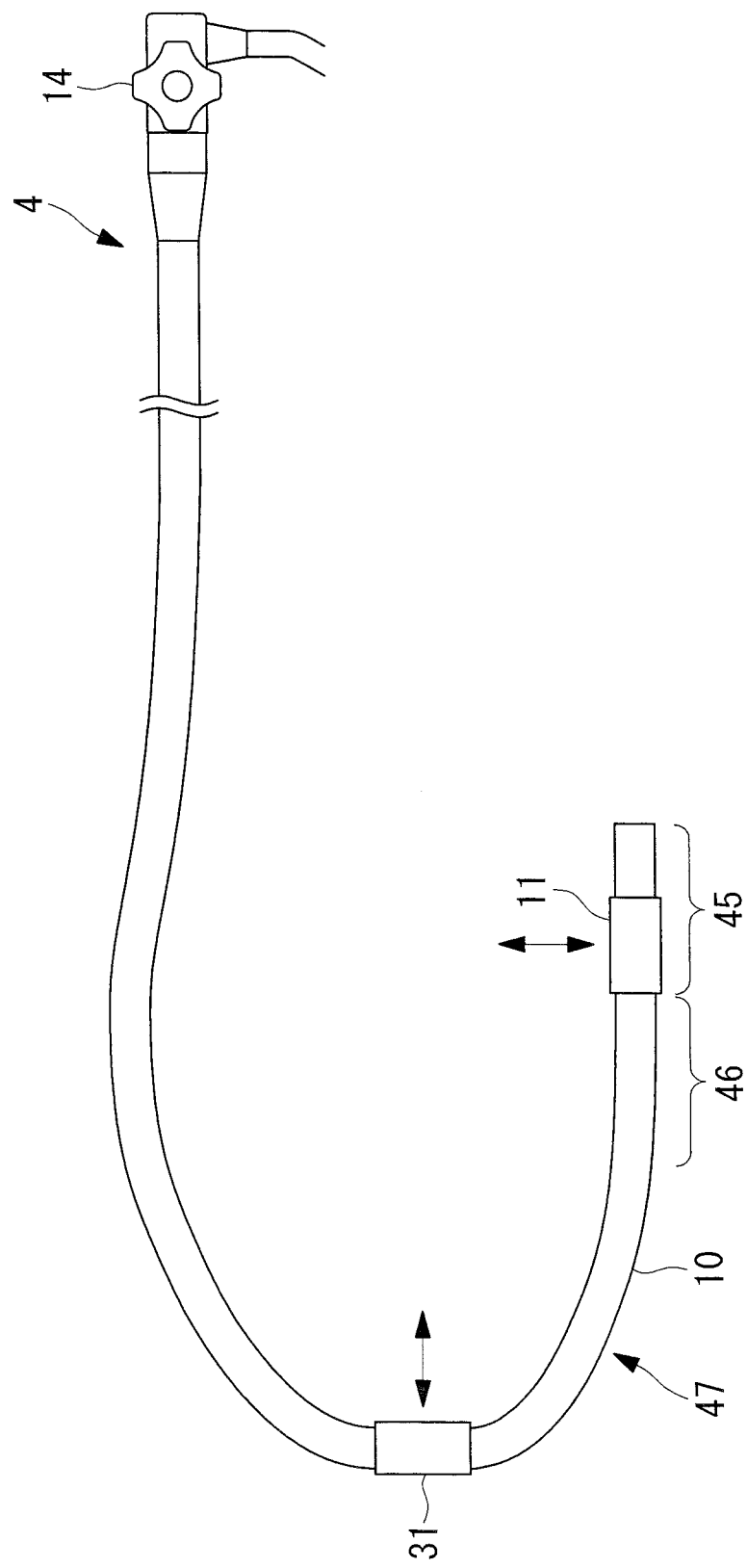
FIG. 17 is a schematic configuration view of an endoscope according to a fourth embodiment of the present invention.

As shown in FIG. 17, in an endoscope 4 according to the present embodiment, the rotor 11 is provided in the rigid portion 45 of the insertion portion 10, and the rotor 31 is provided in the flexible portion 47 of the insertion portion 10.

The endoscope 4 according to the present embodiment is provided with two dials of the rotary operation part 14, which allow the rotors 11 and 31 to be independently rotated.

According to the endoscope 4 of the present embodiment, due to the above configuration, the rotor 11 provided in the rigid portion 45 on the distal end side of the insertion portion 10 and the rotor 31 provided in the flexible portion 47 on the proximal end side of the insertion portion 10 can be independently rotated as necessary. Thus, the insertion portion 10 can be operated in a more complex manner, and the guidable range of the insertion portion 10 inside the pericardial cavity can be further expanded.

(Modified Example)

Figure 18:
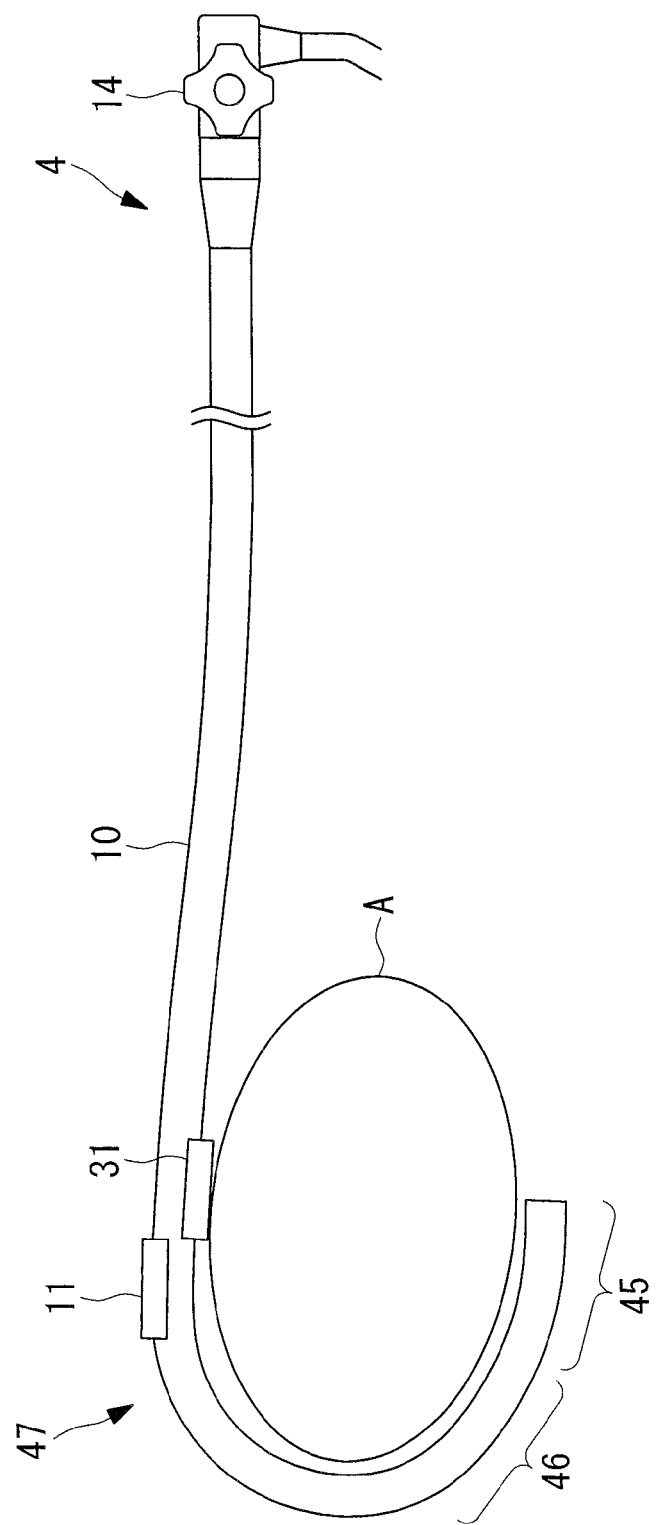
FIG. 18 is a schematic configuration view of an endoscope according to a modified example of FIG. 17.

As shown in FIG. 18, as a modified example of the endoscope 4 according to the present embodiment, the rotors 11 and 31 may be provided only in the flexible portion 47 of the insertion portion 10, without being provided in the rigid portion 45 of the insertion portion 10.

In this connection, for instance, when the insertion portion 10 is wound along the circumference of the heart A in a half circle to one or more circles, the insertion portion 10 is subjected to tension due to its curved shape as a whole, and the movable range of the curving mechanism of the insertion portion 10 becomes smaller. In such a case, the guidable range of the insertion portion 10 can be expanded by providing the rotors 11 and 31 in the flexible portion 47 which comes into contact with the heart A.

Although in this modified example, the example has been described where the rotors 11 and 31 are provided in the flexible portion 47 of the insertion portion 10, only either of the rotors 11 and 31 may be provided in the flexible portion 47 of the insertion portion 10.

{Fifth Embodiment}

Next, an endoscope according to a fifth embodiment of the present invention will be described with reference to the drawings.

Figure 19:
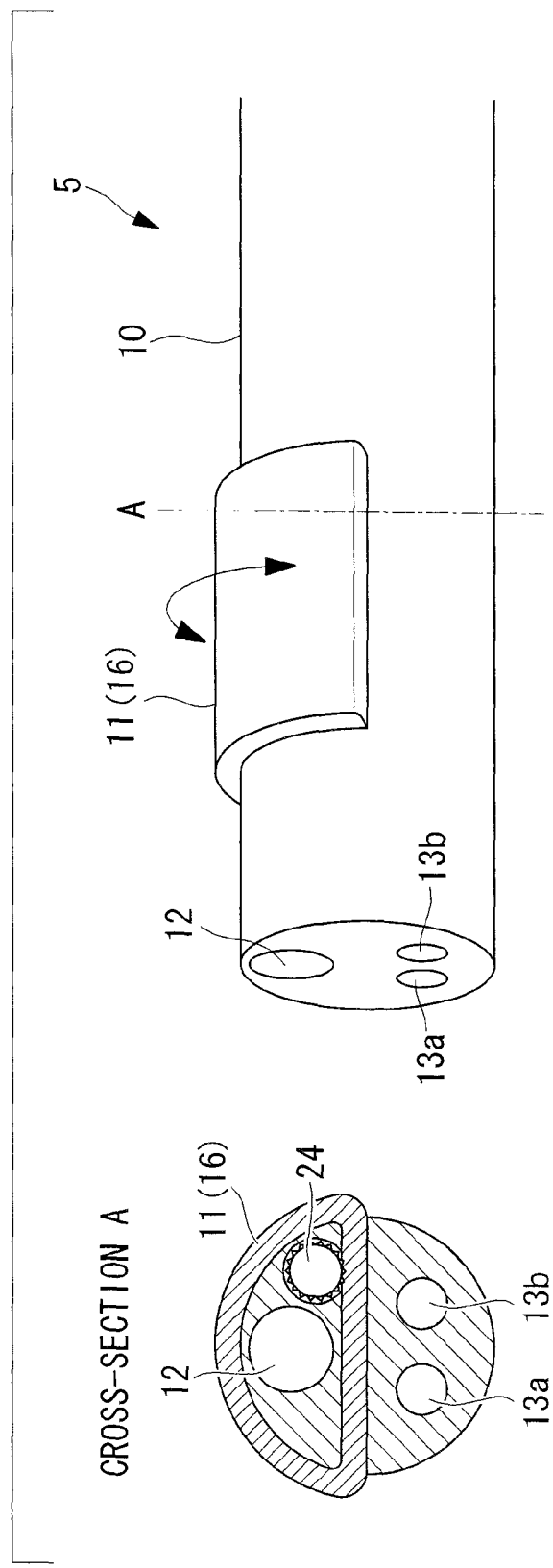
FIG. 19 is a partially enlarged view of an endoscope according to a fifth embodiment of the present invention.

As shown in FIG. 19, in an endoscope 5 according to the present embodiment, the rotor 11 is not a solid cylindrical member, but is instead constituted of a crawler belt (Caterpillar (registered trademark)) made of the flexible elastic member 16.

Specifically, the elastic member 16 is partially exposed in the outer circumferential surface of the insertion portion 10, and the rest is arranged inside the insertion portion 10. The exposed portion of the elastic member 16 occupies approximately a half of the outer circumference of the insertion portion 10 in the circumferential direction of the insertion portion 10.

Furthermore, the inner circumferential surface of the elastic member 16 is formed with furrows (not shown) which mesh with the drive transmission gear 24.

This configuration makes it possible to reliably receive the drive force from the rotary drive unit 20 by the furrows on the inner circumferential surface of the elastic member 16, as well as to transmit the drive force by the flexible elastic member 16, without causing any damage to the inner wall of the body cavity. Thus, the insertion portion 10 can be moved in the direction along the surface of the inner wall of the body cavity (the direction perpendicular to the axis of the insertion portion 10) so as to guide the distal end of the insertion portion 10 to an intended position.

In addition, according to the endoscope 5 of the present embodiment, due to the above configuration, a cross-sectional area of the insertion portion 10 occupied by the rotor 11 can be made smaller, and the insertion portion 10 can be reduced in diameter.

(First Modified Example)

Figure 20:
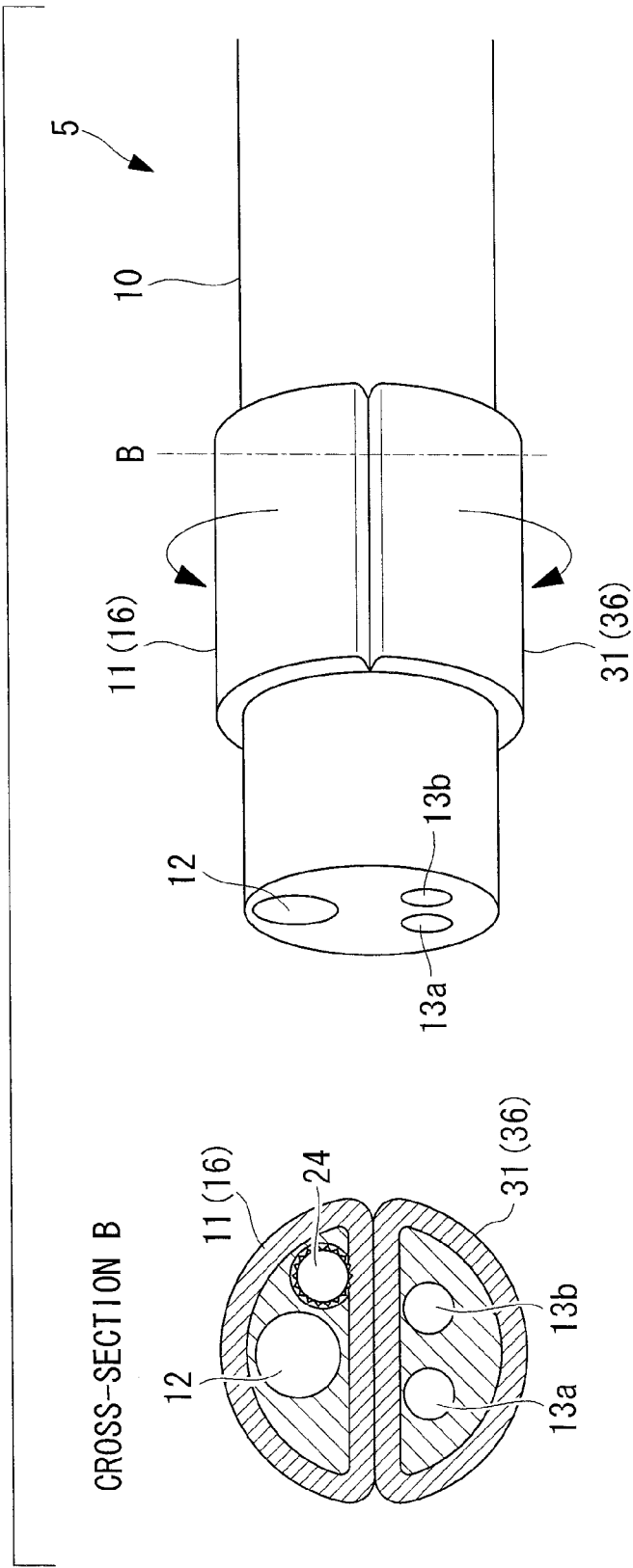
FIG. 20 is a partially enlarged view of an endoscope according to a first modified example of FIG. 19.

As shown in FIG. 20, as a first modified example of the endoscope 5 according to the present embodiment, the plurality of rotors may be arranged symmetrically with respect to the axis of the insertion portion 10.

Specifically, the endoscope 5 according to this modified example includes the rotor 11 constituted of the crawler belt made of the flexible elastic member 16, and the rotor 31 constituted of the crawler belt made of the flexible elastic member 36.

Each of the rotor 11 and the rotor 31 is provided in the outer circumferential surface of the rigid portion 45 of the insertion portion 10 so as to be partially exposed in the outer circumferential surface of the insertion portion 10, and the rest is arranged inside the insertion portion 10. Each of the exposed portions of the elastic members 16 and 36 occupies approximately a half of the outer circumference of the insertion portion 10 in the circumferential direction of the insertion portion 10. Furthermore, the elastic member 16 and the elastic member 36 have their outer circumferential surfaces in close contact with each other inside the insertion portion 10.

Due to this configuration, rotating the rotary operation part 14 causes its drive force to be transmitted by the drive transmission wire 23 to the drive transmission gear 24, causing the rotor 11 (elastic member 16) to rotate. Furthermore, this drive force is transmitted from the rotor 11 (elastic member 16) to the rotor 31 (elastic member 36), causing the rotor 31 (elastic member 36) to rotate in the opposite direction to the rotor 11 (elastic member 16).

According to the endoscope 5 of this modified example, due to the above configuration, the rotors 11 and 31 can be brought into contact with both the heart A and the pericardium B when the insertion portion 10 is inserted into a body cavity such as a pericardial cavity. Thus, the drive force of the rotors 11 and 31 can be applied to both the heart A and the pericardium B, allowing the insertion portion 10 to be more reliably guided to an intended position.

In addition, by rotating the rotor 11 and the rotor 31 in the opposite directions, rotation of the insertion portion 10 itself can be prevented, allowing the insertion portion 10 to be reliably moved in the direction along the surface of the heart A or the pericardium B (the direction perpendicular to the axis of the insertion portion 10).

(Second Modified Example)

Figure 21:
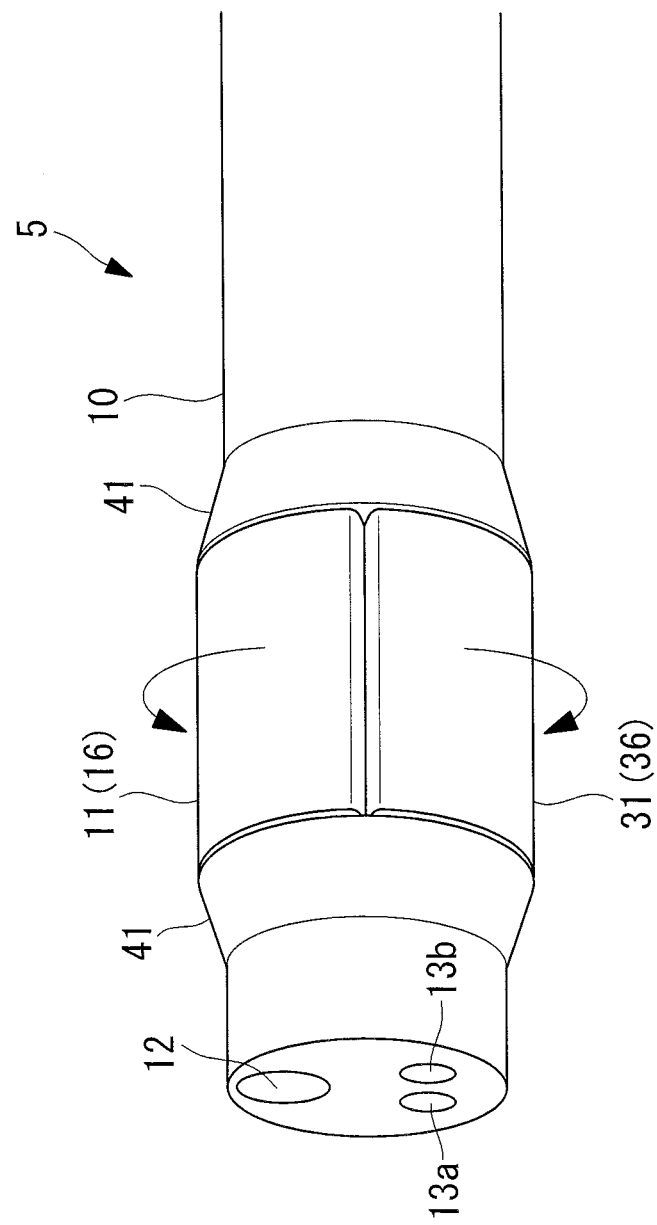
FIG. 21 is a partially enlarged view of an endoscope according to a second modified example of FIG. 19.

As shown in FIG. 21, as a second modified example of the endoscope 5 according to the present embodiment, the cylindrical tapered portions (inclined planes) 41 may be respectively provided in the front-rear direction of the rotor 11 and the rotor 31 (the direction along the axis of the insertion portion 10).

According to the endoscope 5 of this modified example, since the tapered portions 41 are respectively provided in the front-rear direction of the rotor 11 and the rotor 31, the resistance in moving the insertion portion 10 in the axial direction can be reduced, as well as the rotors 11 and 31 can be prevented from getting caught on the inner wall of the body cavity. Thus, the insertion portion 10 can be moved more smoothly in the axial direction.

(Third Modified Example)

Figure 22:
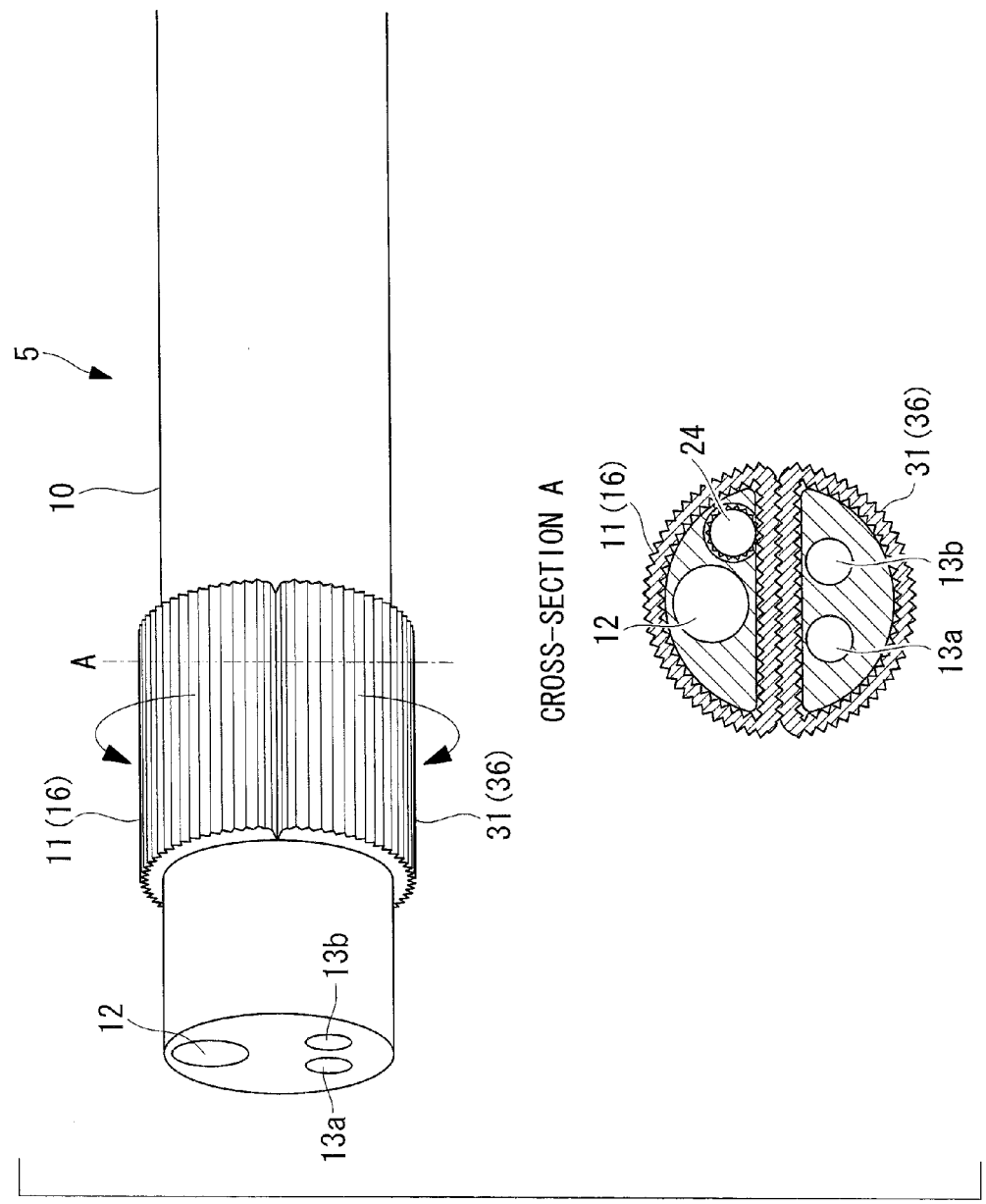
FIG. 22 is a partially enlarged view of an endoscope according to a third modified example of FIG. 19.

As shown in FIG. 22, as a third modified example of the present embodiment, ridges and furrows (projections) may be provided not only on the inner circumferential surfaces of the elastic members 16 and 36, but also on the outer circumferential surfaces of the elastic members 16 and 36.

In the endoscope 5 according to this modified example, the furrows which mesh with the drive transmission gear 24 are formed on the inner circumferential surface of the elastic member 16.

This configuration allows the drive force from the rotary drive unit 20 to be reliably received by the furrows on the inner circumferential surface of the elastic member 16. Thus, the insertion portion 10 can be moved in the direction along the surface of the inner wall of the body cavity (the direction perpendicular to the axis of the insertion portion 10) so as to guide the distal end of the insertion portion 10 to an intended position.

In the endoscope 5 according to this modified example, the ridges and furrows meshing with each other are formed on the outer circumferential surfaces of the elastic members 16 and 36. Furthermore, these ridges and furrows are formed in the direction along the axis of the insertion portion 10.

This configuration allows the drive force from the rotary drive unit 20 to be efficiently transmitted from the rotor 11 (elastic member 16) to the rotor 31 (elastic member 36) by the ridges and furrows formed on the outer circumferential surfaces of the elastic members 16 and 36.

In addition, according to the endoscope 5 of this modified example, due to the above configuration, the frictional resistance between the outer circumferential surfaces of the rotors 11 and 31 and the inner wall of the body cavity can be increased, allowing the drive force of the rotors 11 and 31 to be efficiently transmitted to the inner wall of the body cavity.

Furthermore, since the ridges and furrows on the outer circumferential surfaces of the elastic members 16 and 36 are formed in the direction along the axis of the insertion portion 10, the frictional resistance between the insertion portion 10 and the inner wall of the body cavity can be reduced when moving the insertion portion 10 in the axial direction (during insertion), allowing smooth insertion of the insertion portion 10. On the other hand, when moving the insertion portion 10 in the direction perpendicular to the axis by rotating the rotors 11 and 31, the frictional resistance between the insertion portion 10 and the inner wall of the body cavity can be increased, allowing the drive force of the rotors 11 and 31 to be efficiently transmitted to the inner wall of the body cavity so as to move the insertion portion 10.

{Sixth Embodiment}

Next, an endoscope according to a sixth embodiment of the present invention will be described with reference to the drawings.

Figure 23:
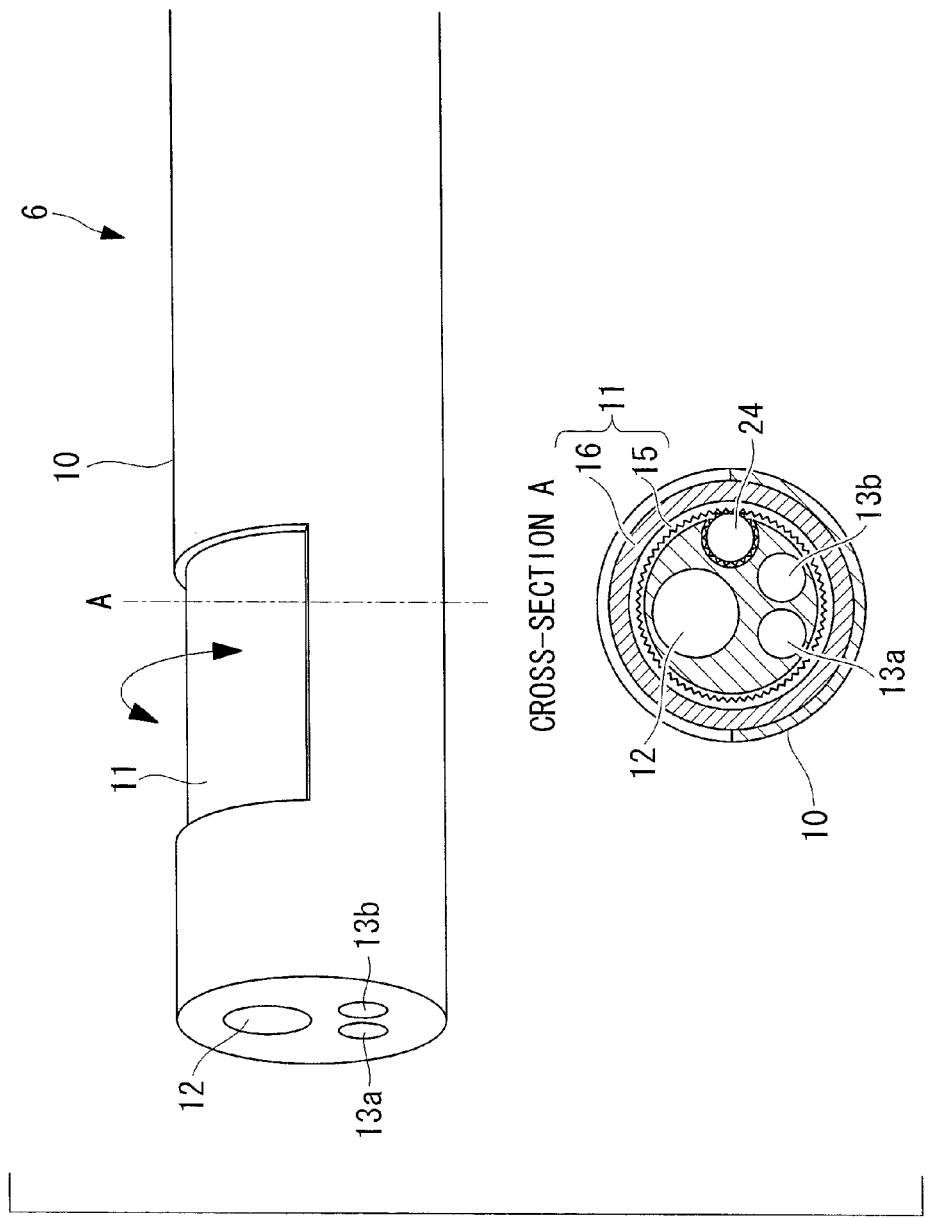
FIG. 23 is a partially enlarged view of an endoscope according to a sixth embodiment of the present invention.

As shown in FIG. 23, in an endoscope 6 of the present embodiment, the rotor 11 is housed further in the inside than the outer circumferential surface of the insertion portion 10.

In the endoscope 6 according to the present embodiment, the rotor 11 has an outer diameter smaller than the outer diameter of the insertion portion 10, and the rotational axis of the rotor 11 is arranged so as to coincide with the central axis of the insertion portion 10.

A window, through which the rotor 11 arranged inside the insertion portion 10 is partially exposed, is formed in the outer circumferential surface of the insertion portion 10.

According to the endoscope 6 of the present embodiment, the drive force of the rotor 11 can be applied either to the heart A or to the pericardium B through the window formed in the outer circumferential surface of the insertion portion 10, allowing the insertion portion 10 to be moved in the direction along the surface of the heart A or the pericardium B (the direction perpendicular to the axis of the insertion portion 10) so as to guide the insertion portion 10 to an intended position.

In addition, according to the endoscope 6 of the present embodiment, since the rotor 11 is housed further in the inside than the outer circumferential surface of the insertion portion 10, the resistance in moving the insertion portion 10 in the axial direction can be made smaller, as well as the rotor 11 can be prevented from getting caught on the inner wall of the body cavity. Thus, the insertion portion 10 can be moved more smoothly in the axial direction.

(Modified Example)

Figure 24:
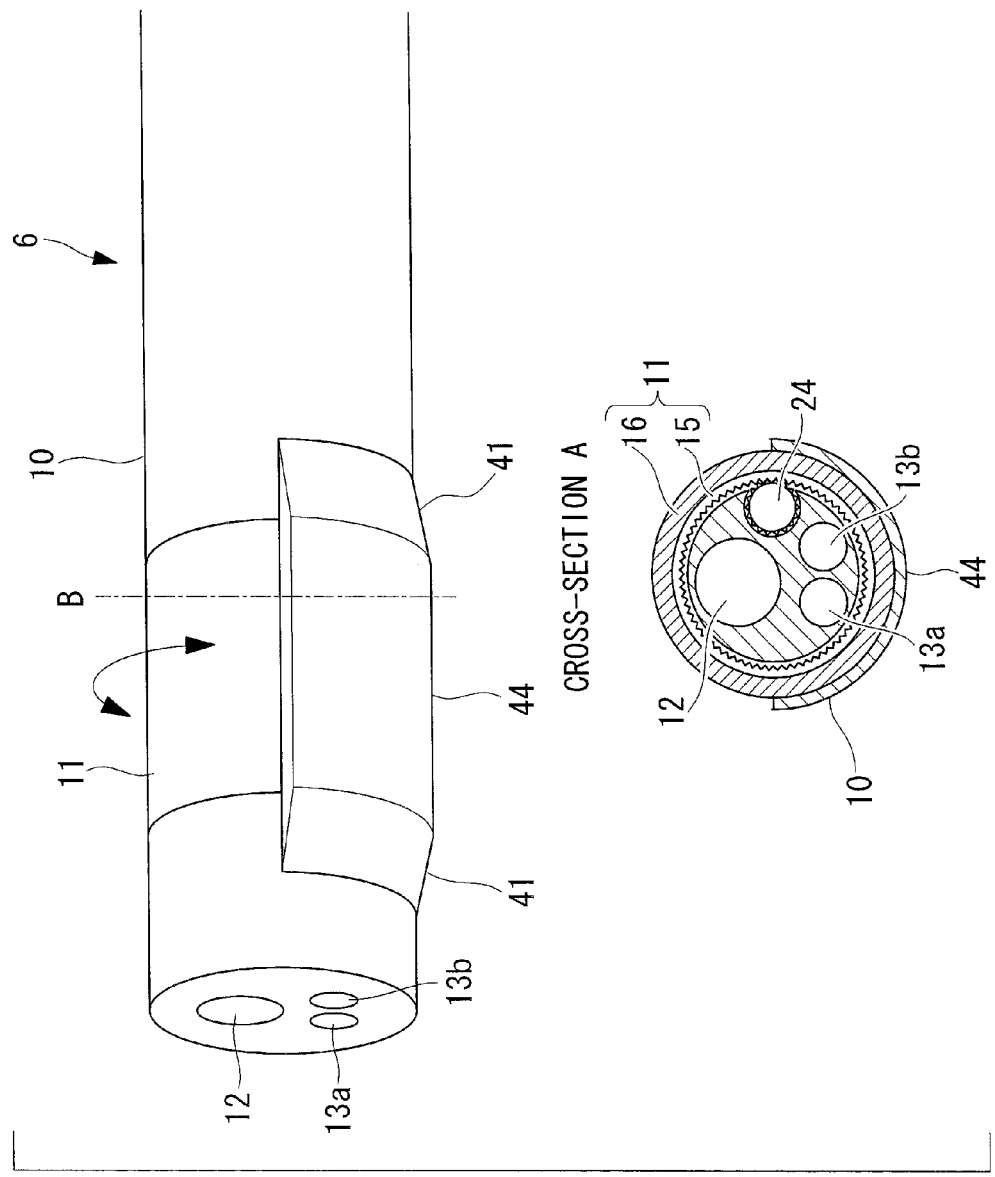
FIG. 24 is a partially enlarged view of an endoscope according to a modified example of FIG. 23.

As shown in FIG. 24, as a modified example of the endoscope 6 according to the present embodiment, the rotor 11 may be partially covered by a shielding plate 44, in place of the window in the outer circumferential surface of the insertion portion 10.

In the endoscope 6 according to this modified example, the rotor 11 has an outer diameter almost equal to the outer diameter of the insertion portion 10.

The shielding plate 44 covers the rotor 11 such that the exposed portion of the rotor 11 occupies approximately a half of the outer circumference of the insertion portion 10 in the circumferential direction of the insertion portion 10. Furthermore, the shielding plate 44 is provided with the tapered portions (inclined planes) 41 in the front-rear direction of the rotor 11 (the direction along the axis of the insertion portion 10).

This configuration can reduce the resistance in moving the insertion portion 10 in the axial direction, as well as can prevent the rotor 11 from getting caught on the inner wall of the body cavity. Thus, the insertion portion 10 can be moved more smoothly in the axial direction.

In the endoscope 6 according to this modified example, the rotor 11 may be larger than the outer diameter of the insertion portion 10.

{Seventh Embodiment}

Next, an endoscope according to a seventh embodiment of the present invention will be described with reference to the drawings.

Figure 25:
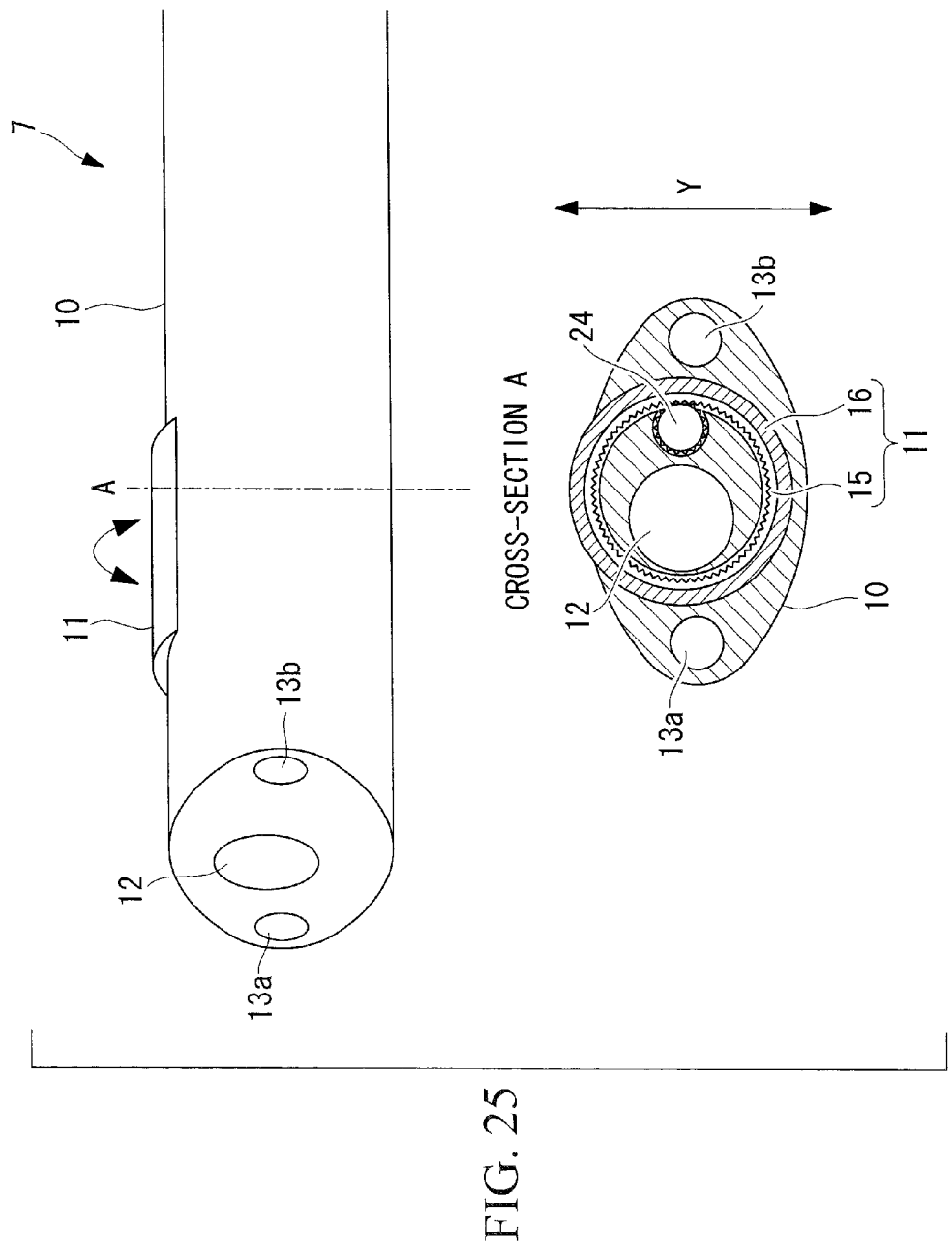
FIG. 25 is a partially enlarged view of an endoscope according to a seventh embodiment of the present invention.

As shown in FIG. 25, in an endoscope 7 according to the present embodiment, the insertion portion 10 has a flat shape and the rotor 11 is exposed in the short axis direction of the transverse section of the insertion portion 10 (the direction indicated by the arrow Y in FIG. 25).

By forming the insertion portion 10 into a flat shape, in a space such as a pericardial cavity where pressure is applied from both directions, from the heart A side as well as from the pericardium B side, the longitudinal direction of the transverse section of the insertion portion 10 is more likely to become parallel to the inner wall of the body cavity (the surface of the heart A or the pericardium B) due to the pressure from both the directions. In this state, by exposing the rotor 11 in the short axis direction of the transverse section of the insertion portion 10, the rotor 11 can be reliably brought into contact with the inner wall of the body cavity so as to transmit the drive force.

(Modified Example)

Figure 26:
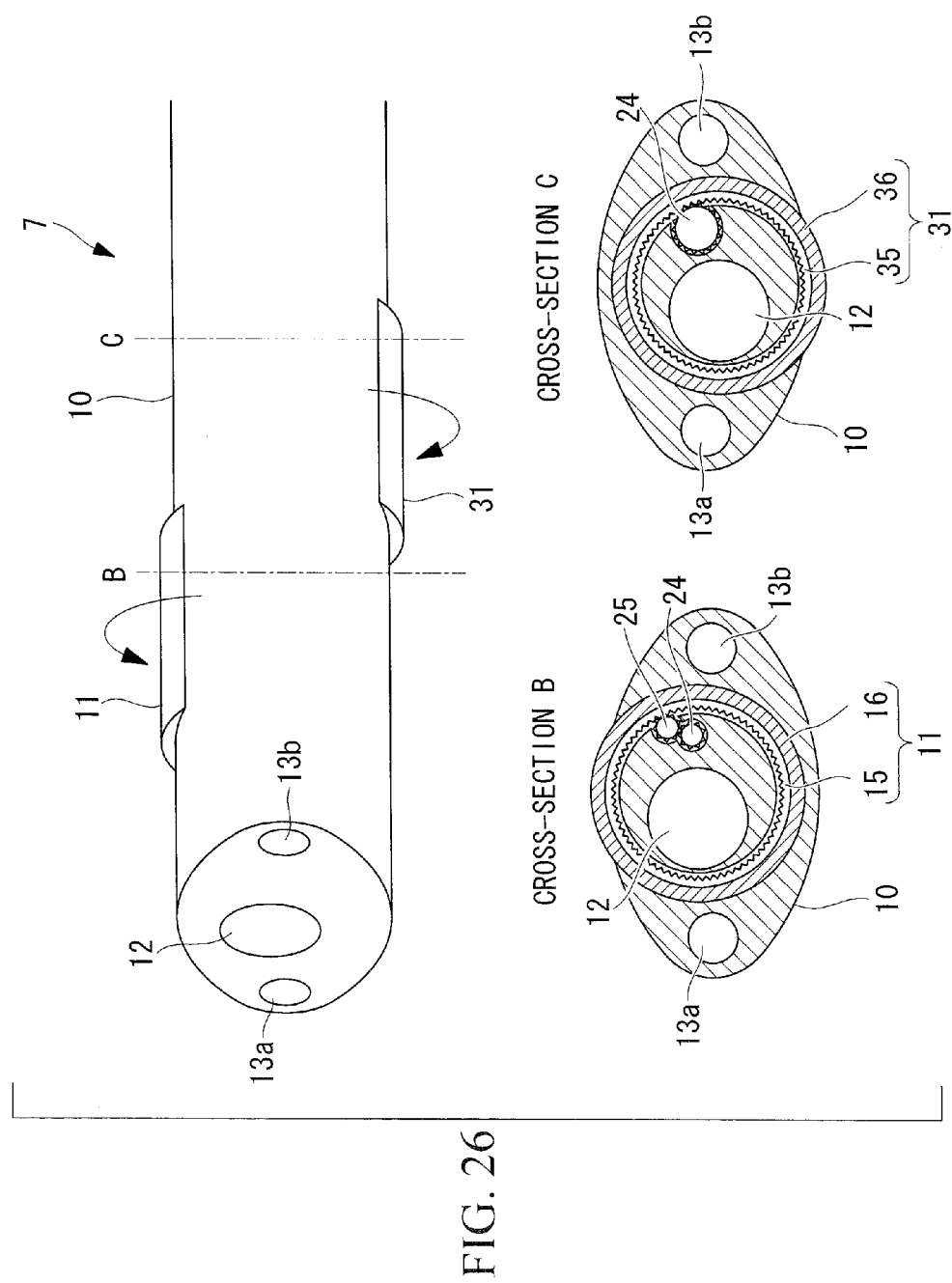
FIG. 26 is a partially enlarged view of an endoscope according to a modified example of FIG. 25.

As shown in FIG. 26, as a modified example of the endoscope 7 according to the present embodiment, the rotor 31 may be provided, in addition to the rotor 11, at a position symmetrical to the rotor 11 with respect to the axis of the insertion portion 10 (in the short axis direction of the transverse section of the insertion portion 10).

Due to the above configuration, when the insertion portion 10 is inserted into a body cavity such as a pericardial cavity, the rotors 11 and 31 can be brought into contact with both the heart A and the pericardium B. Thus, the drive force of the rotors 11 and 31 can be applied to both the heart A and the pericardium B, allowing the insertion portion 10 to be more reliably guided to an intended position.

In addition, by rotating the rotor 11 and the rotor 31 in the opposite directions, rotation of the insertion portion 10 itself can be prevented, allowing the insertion portion 10 to be reliably moved in the direction along the surface of the heart A or the pericardium B (the direction perpendicular to the axis of the insertion portion 10).

{Eighth Embodiment}

Next, an endoscope according to an eighth embodiment of the present invention will be described with reference to the drawings.

Figure 27:
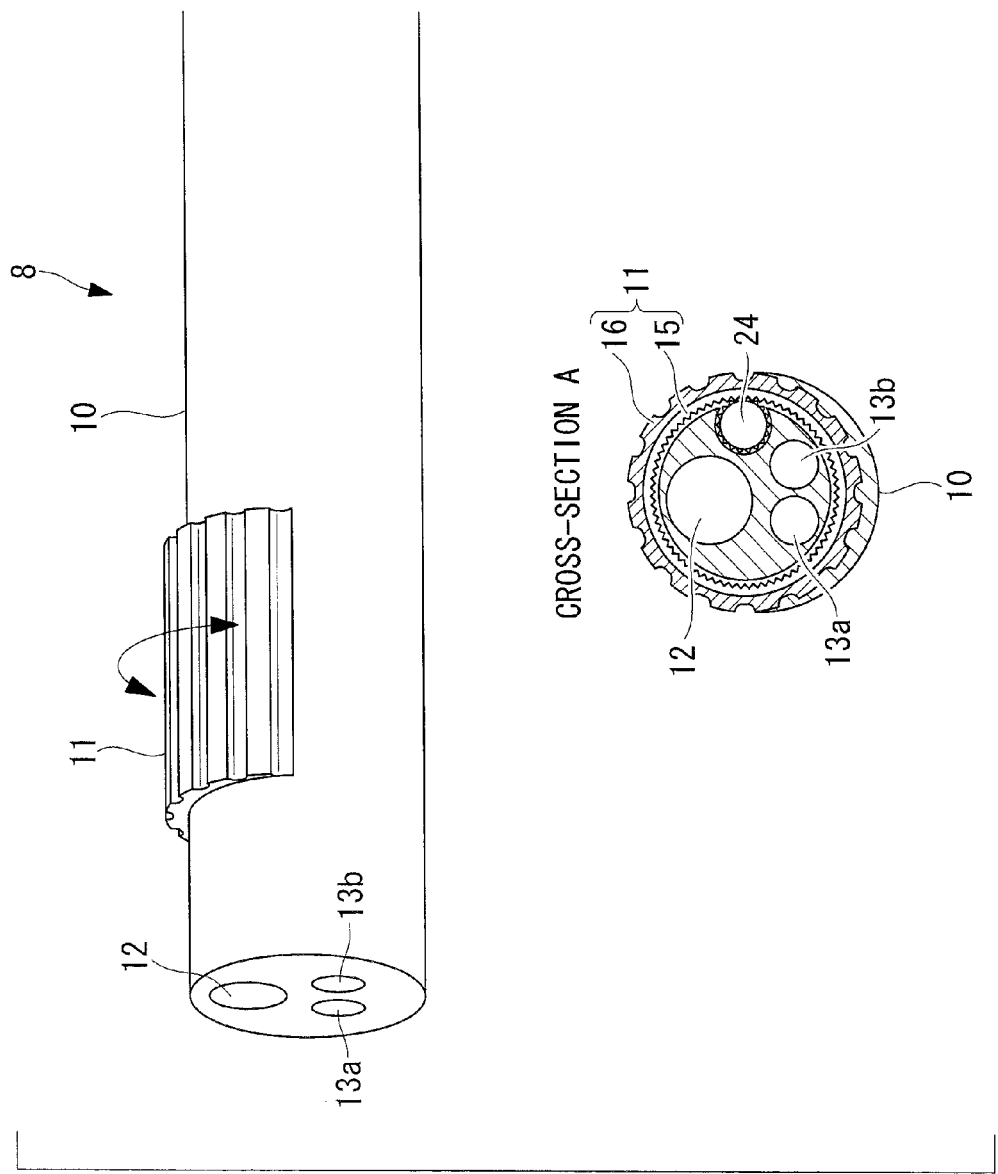
FIG. 27 is a partially enlarged view of an endoscope according to an eighth embodiment of the present invention.

As shown in FIG. 27, in an endoscope 8 according to the present embodiment, the outer circumferential surface of the rotor 11 is formed with ridges and furrows. These ridges and furrows are formed in the direction along the axis of the insertion portion 10.

With this configuration, the frictional resistance between the insertion portion 10 and the inner wall of the body cavity can be reduced when moving the insertion portion 10 in the axial direction (during insertion) to allow the smooth insertion. On the other hand, when moving the insertion portion 10 in the direction perpendicular to the axis by rotating the rotor 11, the frictional resistance between the insertion portion 10 and the inner wall of the body cavity can be increased, allowing the drive force to be efficiently transmitted to the inner wall of the body cavity so as to move the insertion portion 10.

Figure 28:
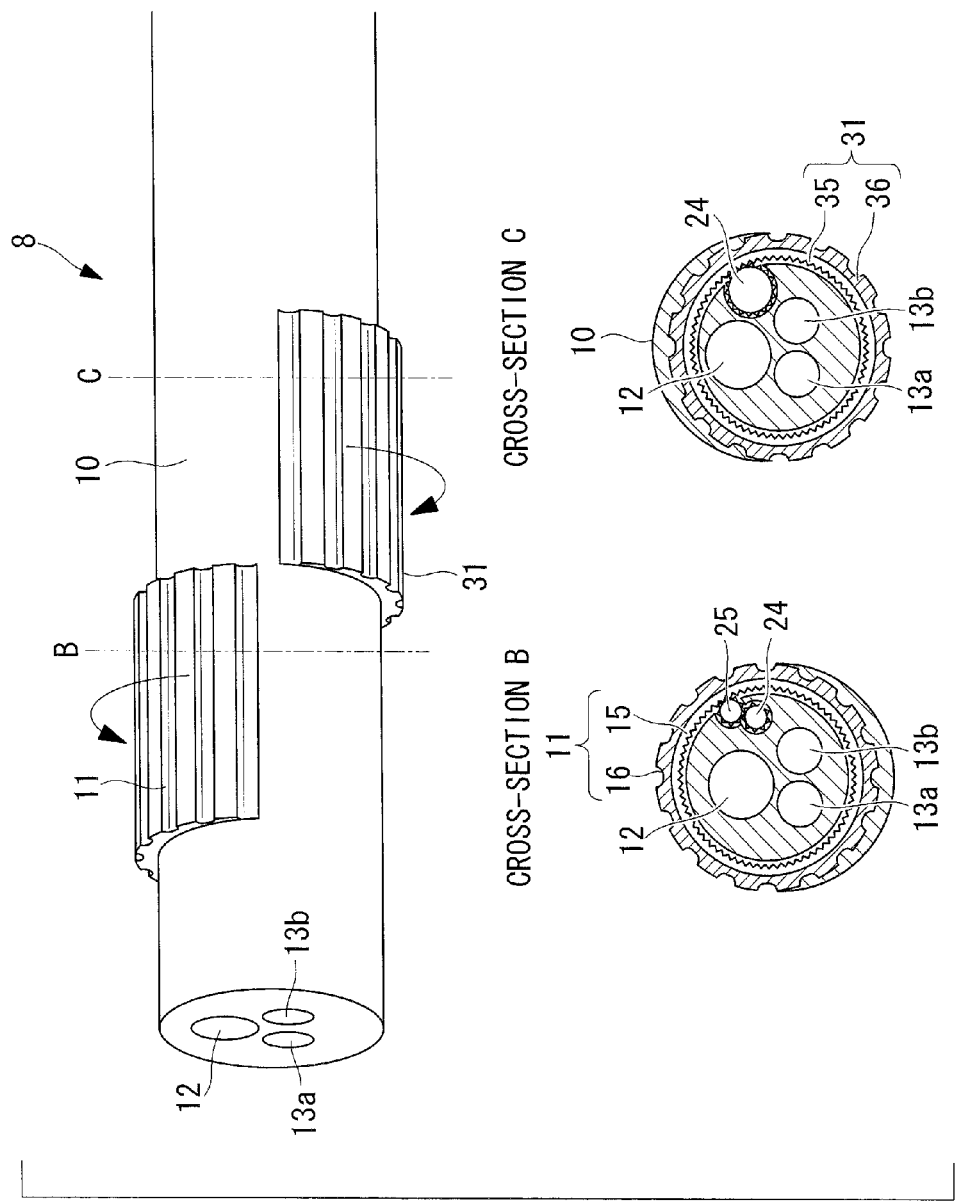
FIG. 28 is a partially enlarged view of an endoscope according to a first modified example of FIG. 27.

As shown in FIG. 28, as a first modified example of the endoscope 8 according to the present embodiment, in a case where the rotors 11 and 31 are provided at positions symmetrical with respect to the axis of the insertion portion 10, the ridges and furrows may be formed on the outer circumferential surfaces of these rotors 11 and 31.

Figure 29:
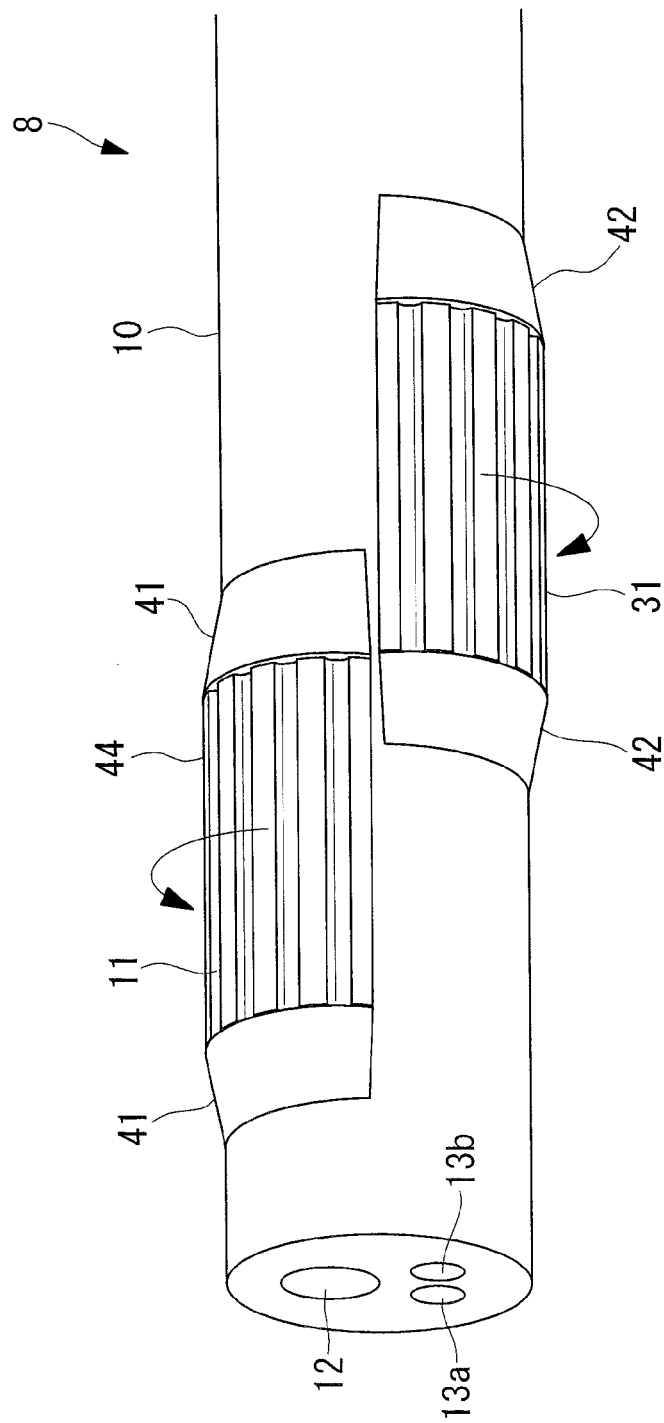
FIG. 29 is a partially enlarged view of an endoscope according to a second modified example of FIG. 27.

Further, as shown in FIG. 29, as a second modified example of the endoscope 8 according to the present embodiment, the rotors 11 and 31 may be respectively provided with the tapered portions 41 and 42 in the front-rear direction (the direction along the axis of the insertion portion 10).

{Ninth Embodiment}

Next, an endoscope according to a ninth embodiment of the present invention will be described with reference to the drawings.

Figure 30:
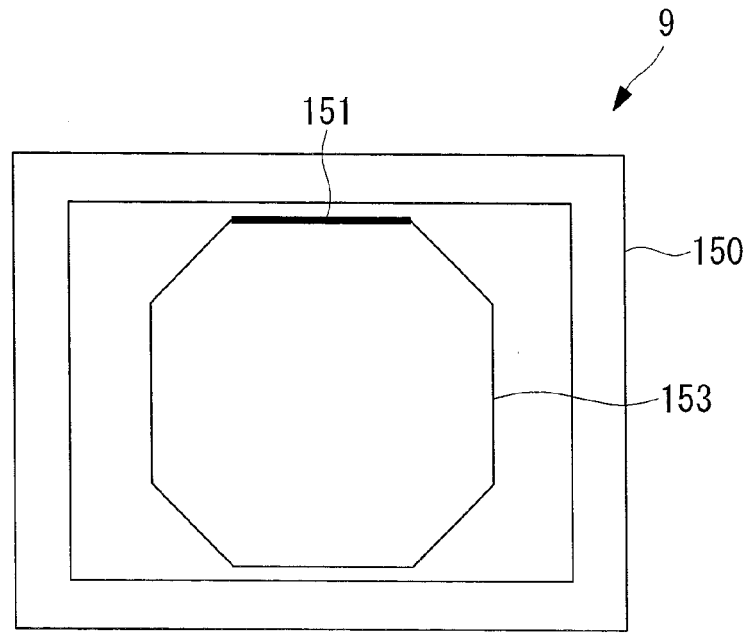
FIG. 30 is an example screen of a display unit of an endoscope according to a ninth embodiment of the present invention.

As shown in FIG. 30, in an endoscope 9 of the present embodiment, a display unit 150 displays a mark indicating a position of the rotor 11 in an image obtained by the camera 12.

Specifically, as shown in FIG. 30, in an image 153 obtained by the camera 12 and displayed in the display unit 150, a mark 151 indicating the position of the rotor 11 is displayed.

As a method for inserting the mark 151, the position may be marked inside an optical system or on a CCD (specifically, by using only one color filter or cutting out some pixels), or the marking data may be superimposed on the image when it is displayed in the display unit 150.

According to the endoscope 9 of the present embodiment, the position of the rotor 11 can be visually checked in the image displayed in the display unit 150, allowing the rotor 11 to be reliably brought into contact with the inner wall of the body cavity so as to guide the distal end of the insertion portion 10 to an intended position.

Figure 31:
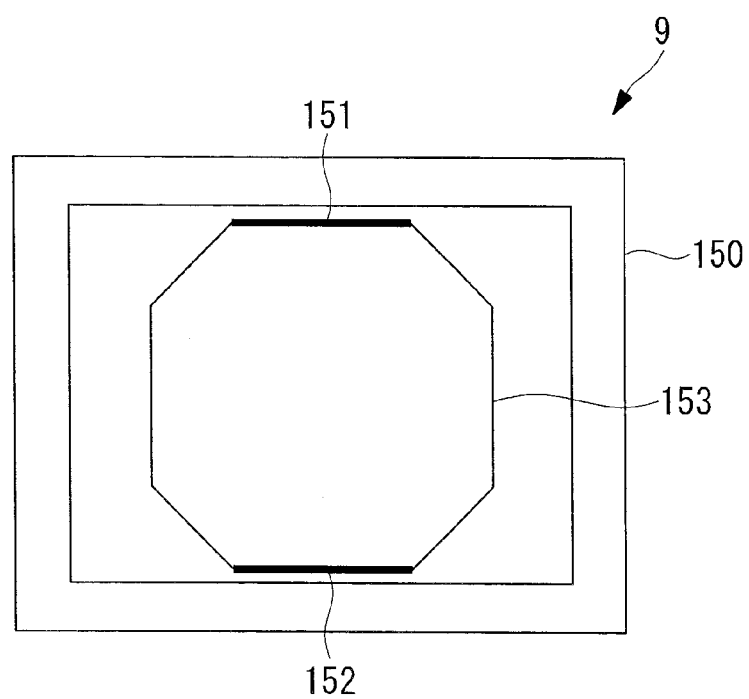
FIG. 31 is an example screen of the display unit of the endoscope according to a modified example of FIG. 30.

As shown in FIG. 31, as a modified example of the endoscope 9 according to the present embodiment, in a case where the plurality of rotors 11 and 31 are provided, the mark 151 and a mark 152 corresponding to the positions of the plurality of rotors 11 and 31 can be displayed.

{Tenth Embodiment}

Next, an endoscope according to a tenth embodiment of the present invention will be described with reference to the drawings.

Figure 32:
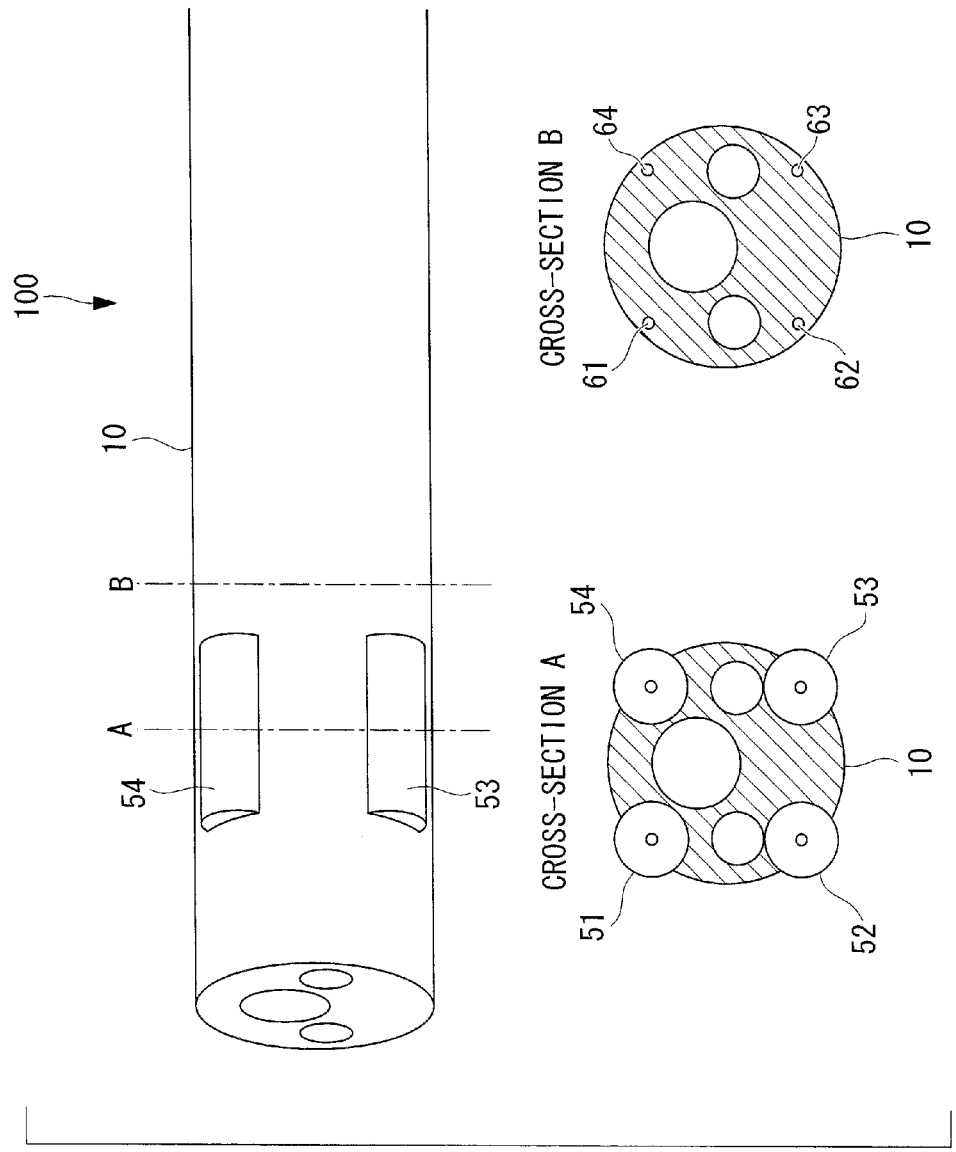
FIG. 32 is a partially enlarged view of an endoscope according to a tenth embodiment of the present invention.

As shown in FIG. 32, an endoscope 100 according to the present embodiment includes four rotors in the rigid portion 45 of the insertion portion 10, and these rotors are arranged symmetrically with respect to the axis of the insertion portion 10.

Specifically, in the outer circumferential surface of the rigid portion 45 of the insertion portion 10, the rotors 51, 52, 53 and 54 having their rotational axes arranged in the direction along the axis of the insertion portion 10 are arranged at regular intervals in the circumferential direction of the insertion portion 10.

Figure 33:
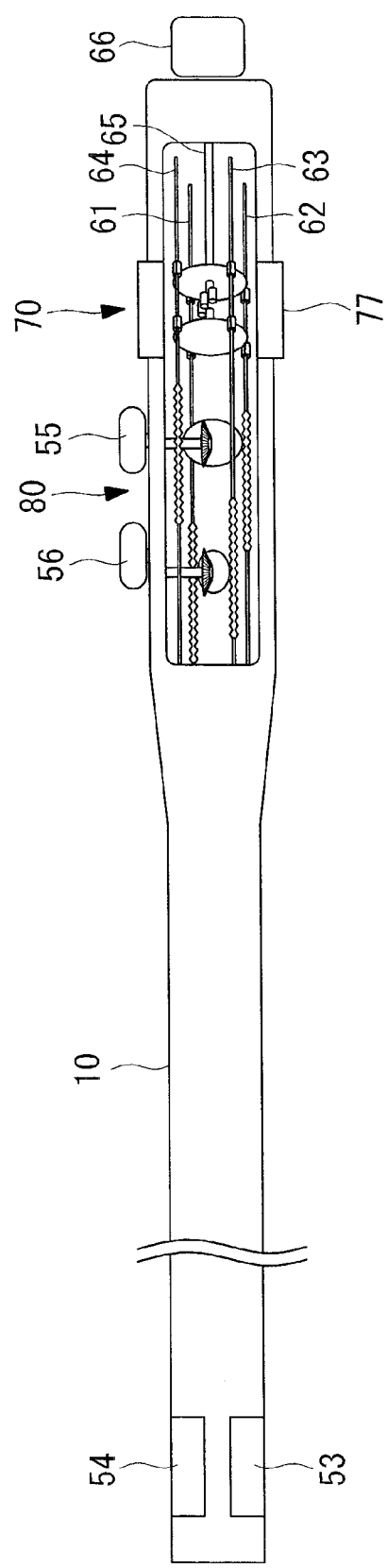
FIG. 33 is a longitudinal cross-sectional view of the endoscope of FIG. 32.

Wires 61, 62, 63, and 64 extending in the direction along the axis of the insertion portion 10 are connected to the rotors 51, 52, 53, and 54, respectively, inside the insertion portion 10. As shown in FIG. 33, these wires 61, 62, 63, and 64 are connected through a rotational direction selecting device 70 and a rotational axis 65 to a rotary operation part 66. Furthermore, these wires 61, 62, 63, and 64 are connected through a curving mechanism 80 to curving operation parts 55 and 56.

Figure 34:
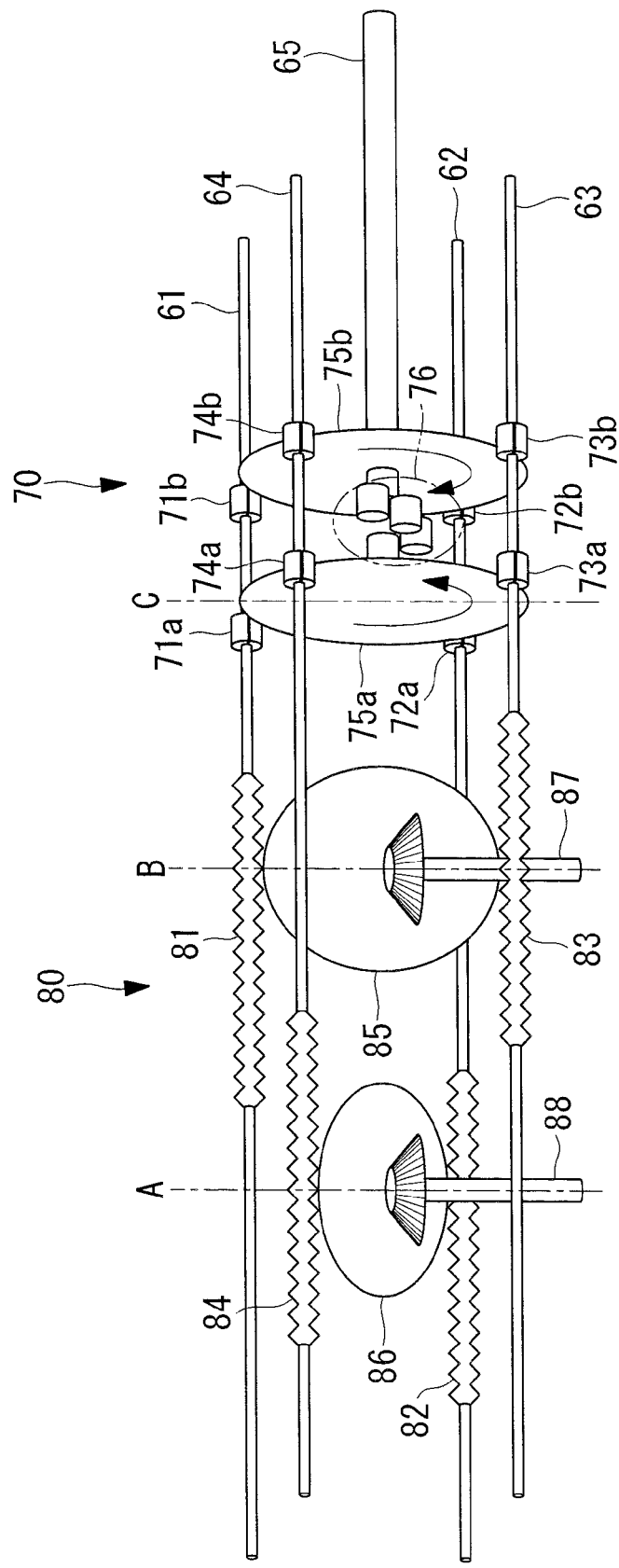
FIG. 34 is a partially enlarged view of the endoscope of FIG. 33.

As shown in FIG. 34, the rotational direction selecting device 70 includes: clutches 71a, 72a, 73a, and 74a provided on the wires 61, 62, 63, and 64, respectively, at the same positions on the axial direction; clutches 71b, 72b, 73b, and 74b arranged at a distance in the axial direction from the clutches 71a, 72a, 73a, and 74a, respectively; a rotary drive plate 75a provided at the same position as the clutches 71a to 74a on the axial direction; a rotary drive plate 75b provided at the same position as the clutches 71b to 74b on the axial direction; a reversing gear 76 provided between the rotary drive plate 75a and the rotary drive plate 75b; and an annular rotational direction selector 77 (see FIG. 33) arranged outside in the radial direction of all these components.

The rotary drive plate 75b is a disc-shaped member connected to the rotary operation part 66 by the rotational axis 65, and operating the rotary operation part 66 causes the rotary drive plate 75b to rotate around the axis of the insertion portion 10.

The rotary drive plate 75a is a disc-shaped member connected through the reversing gear 76 to the rotary drive plate 75b, and due to the motion of the reversing gear 76, rotation of the rotary drive plate 75b causes the rotary drive plate 75a to rotate in an opposite direction to the rotary drive plate 75b.

As will be described later, the clutches 71a to 74a come into contact with the rotary drive plate 75a by being biased inward in the radial direction by the rotational direction selector 77, and rotate in the opposite direction to the rotary drive plate 75a.

As will be described later, the clutches 71b to 74b come into contact with the rotary drive plate 75b by being biased inward in the radial direction by the rotational direction selector 77, and rotate in the opposite direction to the rotary drive plate 75b.

As shown in FIG. 33, the rotational direction selector 77 is arranged on the outer circumferential surface of the insertion portion 10, and is rotatable around the axis of the insertion portion 10.

Figure 38:
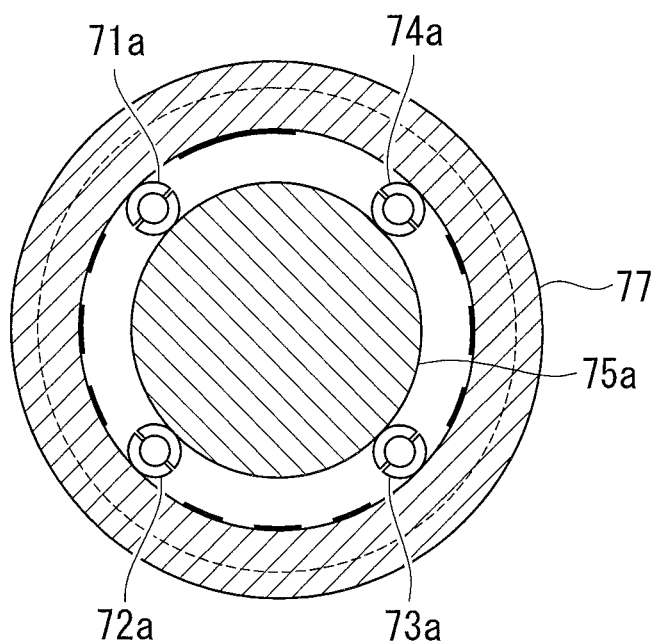
FIG. 38 is a transverse sectional view along the line C of FIG. 34.

FIG. 38 shows a transverse section of the rotational direction selector 77 (the transverse section along the line C in FIG. 34). As shown in FIG. 38, projections (the portions indicated by the thick lines in FIG. 38) projecting inward in the radial direction are partially provided on an inner circumferential surface of the rotational direction selector 77.

These projections bias the clutches 71a to 74a inward in the radial direction and press them against the rotary drive plate 75a. Similarly, these projections bias the clutches 71b to 74b inward in the radial direction and press them against the rotary drive plate 75b. In other words, the clutch for which the projection is arranged outside in the radial direction is connected to the rotary drive plate, while the clutch for which the projection is not arranged outside in the radial direction is disconnected.

Due to the above configuration, connection/disconnection to/from the rotary drive plate is performed on a clutch-by-clutch basis by rotating the rotational direction selector 77 around the axis of the insertion portion 10. Thus, it can be determined which wire to rotate to the right and which wire to rotate to the left, or which wire's rotation to stop. However, all the clutches are disconnected during the curving motion.

As shown in FIG. 34, the curving mechanism 80 includes: wire pulling gears 81, 82, 83, and 84 provided on the wires 61, 62, 63, and 64, respectively; a disc-shaped gear 85 meshing with the wire pulling gears 81 and 83; and a disc-shaped gear 86 meshing with the wire pulling gears 82 and 84. The gear 85 and the curving operation part 55 are connected by a rotational axis 87. The gear 86 and the curving operation part 56 are connected by a rotational axis 88.

Figure 36:
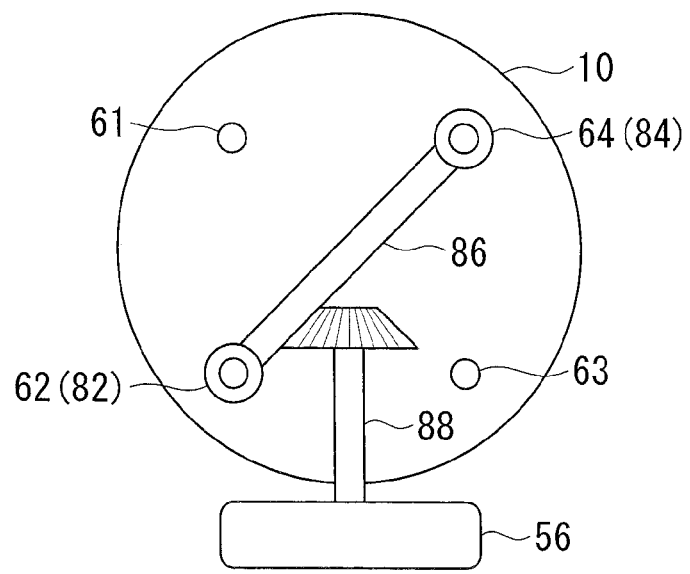
FIG. 36 is a transverse sectional view along the line A of FIG. 34.
Figure 37:
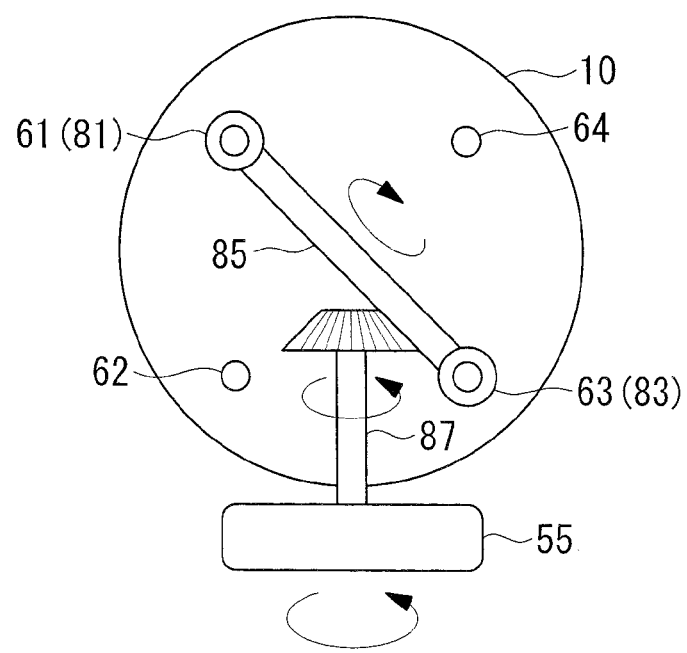
FIG. 37 is a transverse sectional view along the line B of FIG. 34.

FIG. 36 and FIG. 37 respectively show the transverse section along the line A and the transverse section along the line B in FIG. 34.

Figure 35:
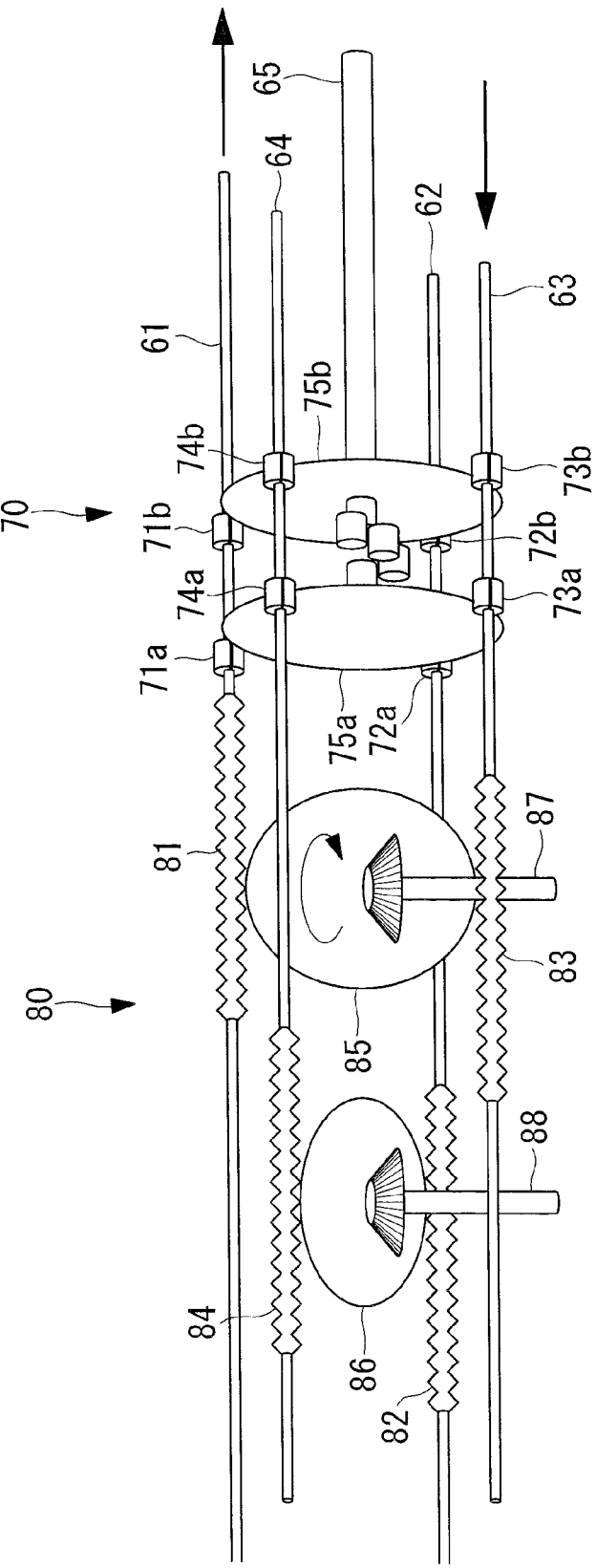
FIG. 35 is a partially enlarged view in a case where a curving mechanism of the endoscope of FIG. 33 is actuated.

For example, as shown in FIG. 37, in the curving mechanism 80 having the above configuration, rotating the curving operation part 55 causes its rotation to be transmitted to the gear 85 through the rotational axis 87. As shown in FIG. 35, this causes the wire pulling gears 81 and 83 meshing with the gear 85 to move in the axial direction. Specifically, the wire pulling gear 81 (wire 61) is moved to a proximal end side, while the wire pulling gear 83 (wire 63) is moved to a distal end side. Thus, the curving portion 46 of the insertion portion 10 is curved.

Similarly, by rotating the curving operation part 56, the wire pulling gear 82 (wire 62) and the wire pulling gear 84 (wire 64) can be moved in the axial direction, and the curving portion 46 of the insertion portion 10 can be curved.

Thus, according to the endoscope 100 of the present embodiment, in addition to the effects similar to those of the endoscope including the plurality of rotors (e.g., the endoscope 2 according to the second embodiment), since the curving motion and the motion of moving perpendicular to the axis can be operated using the same wires, the cross-sectional area of the insertion portion 10 can be made smaller. As this allows the insertion portion to be reduced in diameter, less invasive treatment is possible.

{Eleventh Embodiment}

Next, an eleventh embodiment of the present invention will be described with reference to the drawings. In the present embodiment, an embodiment where the present invention is applied to a sheath for introducing a treatment tool will be described.

Figure 39:
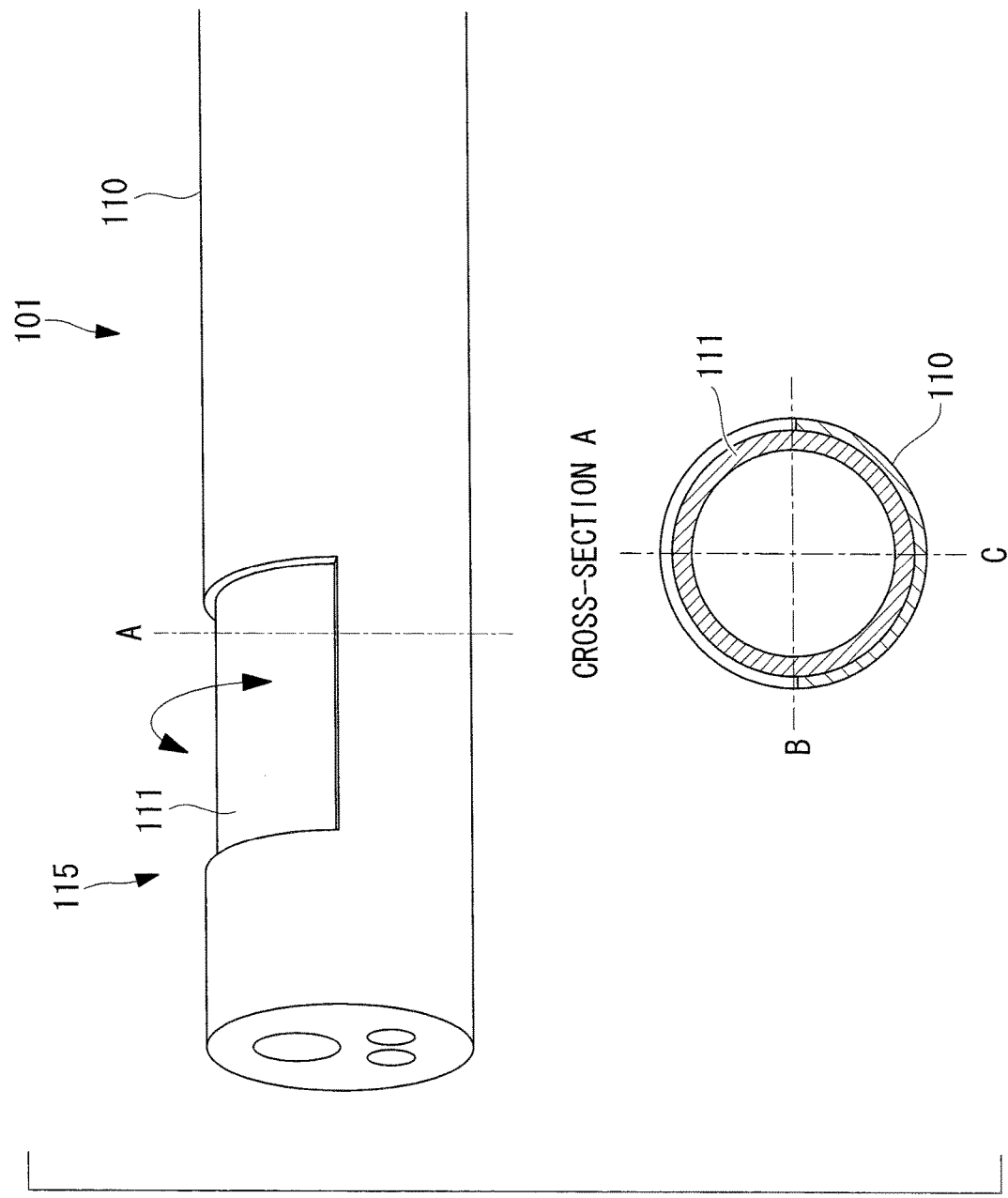
FIG. 39 is a partially enlarged view of a sheath according to an eleventh embodiment of the present invention.
Figure 40:
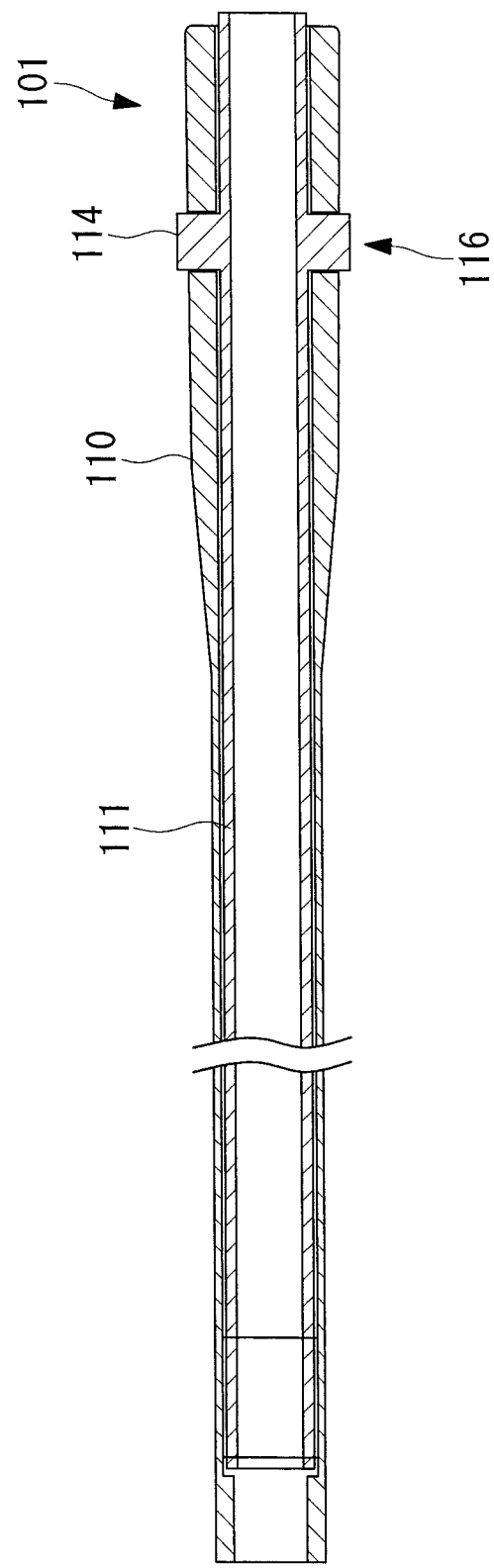
FIG. 40 is a longitudinal cross-sectional view along the line B of FIG. 39.

As shown in FIG. 39, a sheath 101 according to the present embodiment is a cylindrical member which guides a treatment tool, etc. to be inserted into a body cavity. FIG. 40 shows the cross-section B of FIG. 39, and FIG. 41 shows the cross-section C of FIG. 39.

Figure 41:
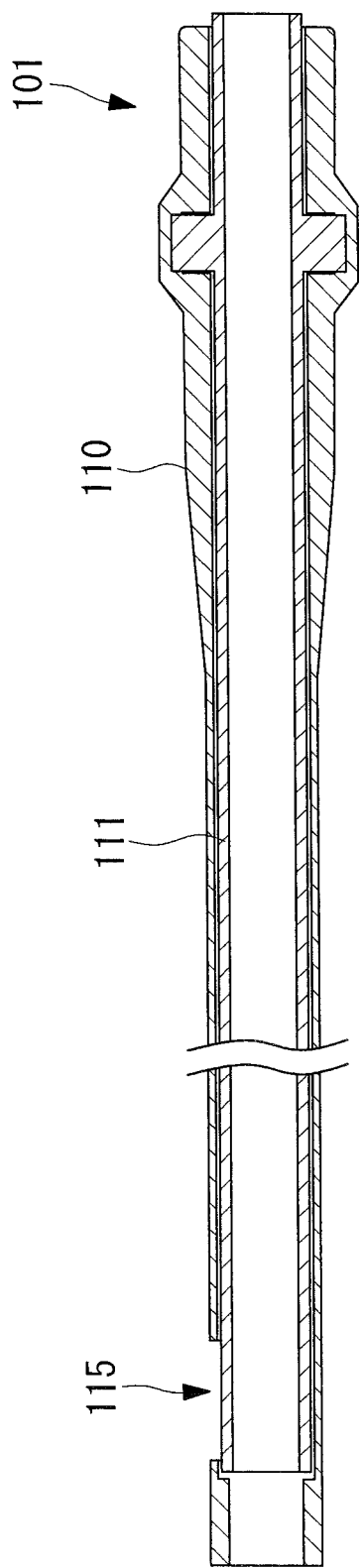
FIG. 41 is a longitudinal cross-sectional view along the line C of FIG. 39.

As shown in FIG. 40 and FIG. 41, the sheath 101 according to the present embodiment includes a cylindrical sheath body 110 and a cylindrical rotor 111 arranged inside the sheath body 110.

The sheath body 110 and the rotor 111 are rotatable relative to each other around the axis. The rotor 111 is arranged so that its rotational axis coincides with a central axis of the sheath body 110.

A window 115, through which the rotor 111 arranged inside the sheath body 110 is partially exposed, is formed in an outer circumferential surface on a distal end side of the sheath body 110.

Furthermore, an opening 116 is provided in the outer circumferential surface on a proximal end side of the sheath body 110. A rotary operation part 114 which protrudes outward in a radial direction and is exposed through the opening 116 of the sheath body 110 is provided on a distal end side of the rotor 111.

Due to this configuration, rotating the rotary operation part 114 around the axis of the sheath body 110 causes the rotor 111 inside the sheath body 110 to rotate around the axis of the sheath body 110 relative to the sheath body 110.

According to the sheath 101 of the present embodiment, the drive force of the rotor 111 can be applied to an inner wall of a body cavity through the window 115 formed in the outer circumferential surface of the sheath body 110, allowing the sheath body 110 to be moved in the direction along a surface of the inner wall of the body cavity (the direction perpendicular to the axis of the insertion portion 10) so as to guide the sheath body 110 to an intended position.

In addition, according to the sheath 101 of the present embodiment, since the rotor 111 is housed further in the inside than the outer circumferential surface of the sheath body 110, it is possible to reduce the resistance in moving the sheath body 110 in the axial direction, as well as to prevent the rotor 111 from getting caught on the inner wall of the body cavity. Thus, the sheath body 110 can be inserted more smoothly into the body cavity.

In the sheath 101 according to the present embodiment, the sheath body 110 may be entirely constituted of a rigid material, or be constituted of a flexible material such as a synthetic resin. In a case where the sheath body 110 is constituted of a flexible material, by using a coil-shaped wire as a portion of the rotor 111 corresponding to the flexible portion, the drive force can be properly transmitted and the rotary operation can be made reliable.

{Twelfth Embodiment}

Next, a twelfth embodiment of the present invention will be described with reference to the drawings. In the following, a sheath of the present embodiment will be descried mainly in terms of differences from the previously described embodiment, while similarities thereto will be denoted by the same reference signs and not described.

Figure 42:
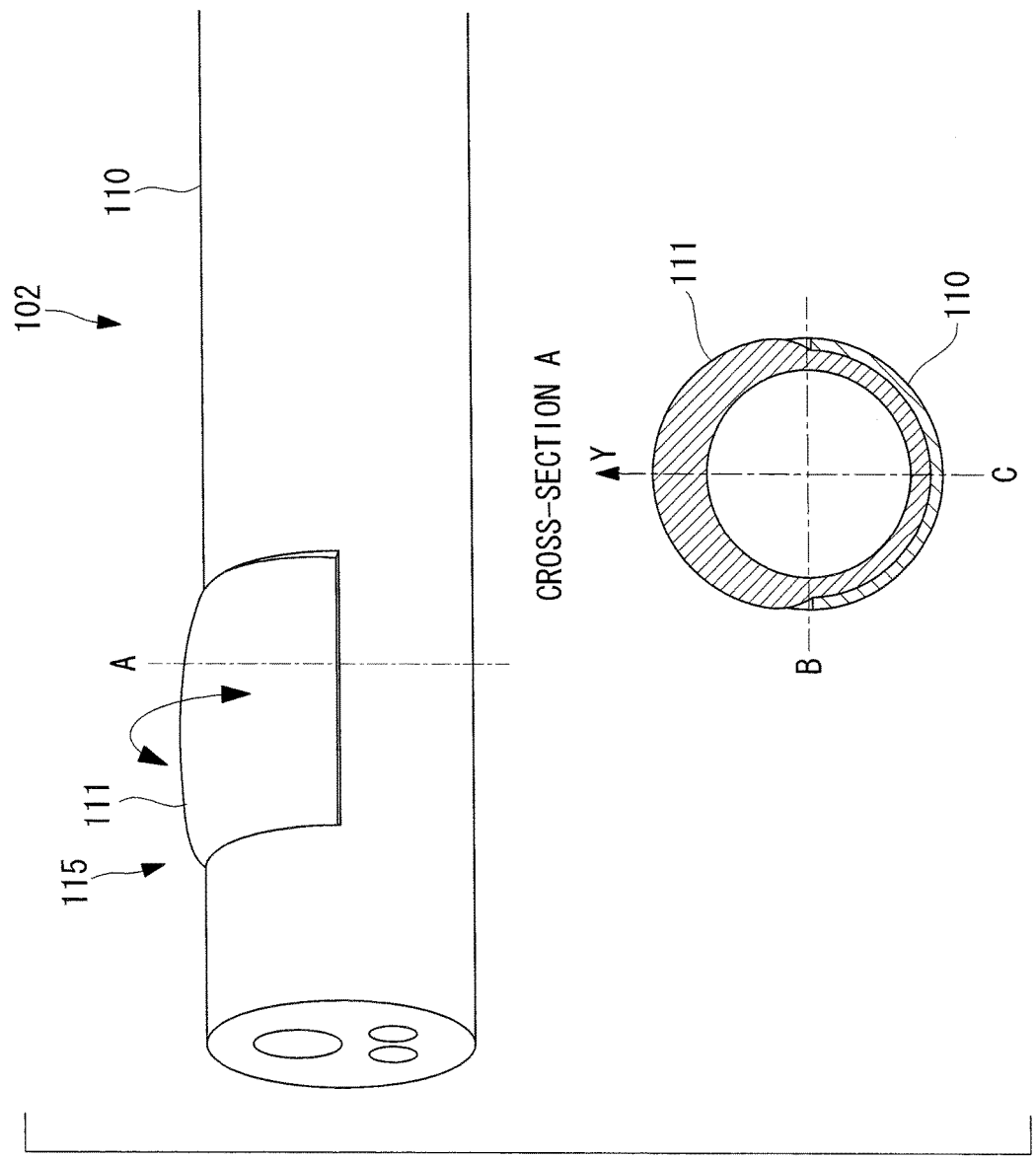
FIG. 42 is a partially enlarged view of a sheath according to a twelfth embodiment of the present invention.
Figure 43:
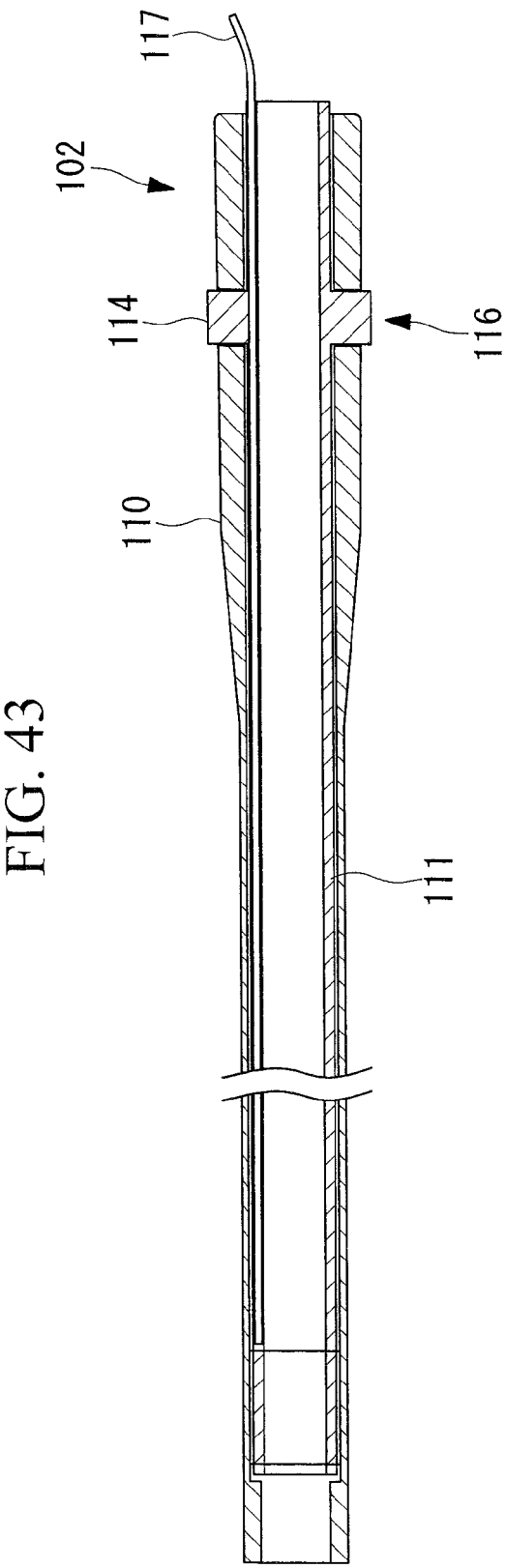
FIG. 43 is a longitudinal cross-sectional view along the line B of FIG. 42.
Figure 44:
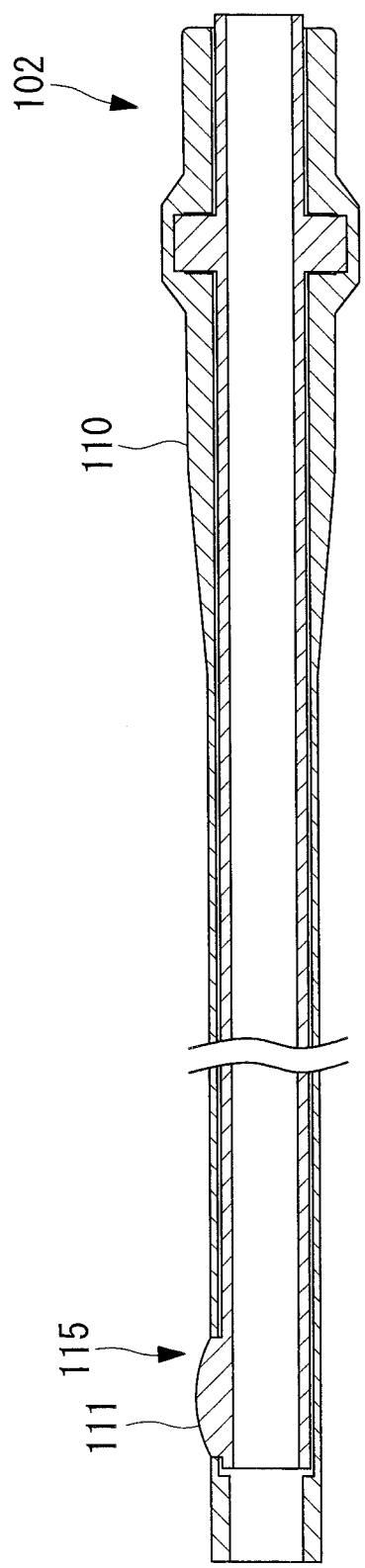
FIG. 44 is a longitudinal cross-sectional view along the line C of FIG. 42.

As shown in FIGS. 42 to 44, a sheath 102 according to the present embodiment includes the cylindrical sheath body 110 and the rotor 111 arranged inside the sheath body 110.

The sheath body 110 and the rotor 111 are formed to be rotatable relative to each other around the axis. The rotor 111 is arranged so that its rotational axis coincides with the central axis of the sheath body 110.

The window 115, through which the rotor 111 arranged inside the sheath body 110 is partially exposed, is formed in the outer circumferential surface on the distal end side of the sheath body 110.

The rotor 111 is constituted of a balloon which increases its volume by the air being blown into an inside thereof. A blower tube 117 for sending the air to the inside of the rotor 111 is connected to an end of the rotor 111 on the distal end side and can apply required pressure.

Due to this configuration, the rotor 111 can expand from the window 115 formed in the outer circumferential surface of the sheath body 110 outward in the radial direction of the sheath body 110 (the direction indicated by the arrow Y in FIG. 42) by the air blown to the inside thereof through the blower tube 117.

Thus, even when the rotor 111 and an outer diameter of the treatment tool are on the same axis, the rotor 111 can protrude outward from the outer diameter of the treatment tool, allowing the force from the rotor 111 to be efficiently transmitted to the outside without any special mechanism being provided for offsetting the axes of the sheath body 110 and the rotor 111.

According to the sheath 102 of the present embodiment, the sheath body 110 can be smoothly inserted into the body cavity by contracting the rotor 111. Furthermore, by expanding the rotor 111 inside the body cavity, the rotor 111 can be more reliably brought into contact with the inner wall of the body cavity, allowing the drive force of the rotor 111 to be efficiently transmitted to the inner wall of the body cavity so as to move the sheath body 110 in the direction perpendicular to the axis.

The embodiments and their modified examples of the present invention have been described above in detail with reference to the drawings. It is intended, however, that the specific configurations are not limited to these embodiments but include design changes, etc. that do not depart from the scope of the present invention. For example, the present invention may be applied to an embodiment which is an appropriate combination of the embodiments and the modified examples.

Furthermore, in the embodiments, the examples have been described where the present invention is applied to the endoscope or the sheath. It is intended, however, that the present invention is not limited to these examples, and the present invention can be applied to other medical instruments, such as an ultrasonic treatment apparatus, a treatment tool, and a catheter, which include an insertion portion to be inserted into a body cavity.

Moreover, in the embodiments, the examples have been described where one, two, or four rotors are provided, but three or five or more rotors may be provided.

REFERENCE SIGNS LIST

A Heart
B Pericardium
1, 2, 3, 4, 5, 6, 7, 8, 9, 100 Endoscope
10 Insertion portion
11, 31, 51, 52, 53, 54 Rotor
12 Camera (imaging unit)
13a Light guide
13b Forceps channel
14 Rotary operation part
15, 35 Cylindrical member
16, 36 Elastic member
20 Rotary drive unit
21, 22 Gear
23 Drive transmission wire
24, 25 Drive transmission gear
45 Rigid portion
46 Curving portion
47 Flexible portion
101, 102 Sheath
150 Display unit

The invention claimed is:

1. A medical instrument, comprising:
an insertion portion which is inserted into a body cavity in an insertion direction;
a rotor which has substantially cylindrical shape and which is provided in an outer circumferential surface of the insertion portion and has its rotational axis arranged parallel to a longitudinal axis of the insertion portion, the longitudinal axis being in the insertion direction of the insertion portion and the rotor having a contact area for contacting an inner wall of the body cavity; and
a rotary drive unit which rotates the rotor around the rotational axis,
wherein rotation of the rotor around the rotational axis by the rotary drive unit causes the contact area to transmit a driving force to the inner wall of the body cavity to move the insertion portion in a direction perpendicular to the longitudinal axis of the insertion portion along the inner wall of the body cavity;
the rotational axis of the rotor and the longitudinal axis of the insertion portion are offset from each other in a radial direction of the insertion portion, and
a turning radius of the rotor is not more than a radius of the insertion portion.

2. The medical instrument according to claim 1, wherein the rotor is provided so as to be partially exposed in the outer circumferential surface of the insertion portion.

3. The medical instrument according to claim 1, further comprising a curving portion which is provided in the insertion portion and curves the insertion portion.

4. The medical instrument according to claim 3, wherein a rigid portion is provided further on a distal end side than the curving portion, and
the rotor is provided in the rigid portion.

5. The medical instrument according to claim 4, wherein a plurality of the rotors are provided in the rigid portion of the insertion portion.

6. The medical instrument according to claim 5, wherein the plurality of rotors are arranged symmetrically with respect to the axis of the insertion portion.

7. The medical instrument according to claim 3, wherein a flexible portion is provided further on a proximal end side than the curving portion of the insertion portion, and
the rotor is provided in the flexible portion.

8. The medical instrument according to claim 1, wherein the rotor protrudes outward in a radial direction from the outer circumferential surface of the insertion portion.

9. The medical instrument according to claim 8, further comprising an inclined plane which is formed between the outer circumferential surface of the insertion portion and an outer circumferential surface of the rotor.

10. The medical instrument according to claim 1, wherein an exposed portion of the rotor occupies approximately a half of an outer circumference of the insertion portion in a circumferential direction of the insertion portion.

11. The medical instrument according to claim 1, wherein the rotor is constituted of a rigid cylindrical member to which a drive force from the rotary drive unit is transmitted, and a flexible elastic member which is provided outside the cylindrical member.

12. The medical instrument according to claim 1, wherein the rotor is a crawler belt constituted of a flexible elastic member.

13. The medical instrument according to claim 1, wherein projections are provided on the outer circumferential surface of the rotor.

14. The medical instrument according to claim 13, wherein the projections are formed in a direction along the axis of the insertion portion.

15. The medical instrument according to claim 1, further comprising a wire which is arranged in an axial direction inside the insertion portion and is connected to the rotational axis of the rotor.

16. The medical instrument according to claim 15, further comprising a rotary operation part which is arranged on the proximal end side of the insertion portion and rotates the wire around the axis.

17. The medical instrument according to claim 1, wherein the insertion portion has a flat shape, and the rotor is exposed in a short axis direction of a transverse section of the insertion portion.

18. The medical instrument according to claim 1, wherein the rotor expands outward in a radial direction of the insertion portion.

19. The medical instrument according to claim 1, wherein the rotary drive unit includes a plurality of gears having different numbers of teeth which transmit a drive force to the rotor.

20. The medical instrument according to claim 1, further comprising an imaging unit which is provided at the distal end of the insertion portion and obtains an image of an inside of the body cavity.

21. The medical instrument according to claim 20, further comprising a display unit which displays the image obtained by the imaging unit, wherein
the display unit displays a mark which indicates a position of the rotor in the image obtained by the imaging unit.

* * * * *